US012251466B2

(12) United States Patent
Bassett et al.

(10) Patent No.: US 12,251,466 B2
(45) Date of Patent: Mar. 18, 2025

(54) SINGLE SOLUTION HYDROGELS WITH COVALENT BONDING FORMED IN SITU, COMPOSITION DESIGN AND MEDICAL PROCEDURES USING THE HYDROGELS

(71) Applicant: Pramand LLC, Bedford, MA (US)

(72) Inventors: Michael Bassett, Hampton, NH (US); Pria Sawhney, Lexington, MA (US)

(73) Assignee: Pramand LLC, Bedford, MA (US)

( * ) Notice: Subject to any disclaimer, the term of this patent is extended or adjusted under 35 U.S.C. 154(b) by 128 days.

(21) Appl. No.: 17/725,361

(22) Filed: Apr. 20, 2022

(65) Prior Publication Data
US 2023/0338286 A1   Oct. 26, 2023

(51) Int. Cl.
| | | |
|---|---|---|
| *A61L 24/00* | (2006.01) | |
| *A61K 9/06* | (2006.01) | |
| *A61K 45/06* | (2006.01) | |
| *A61K 47/08* | (2006.01) | |
| *A61K 47/34* | (2017.01) | |
| *A61L 26/00* | (2006.01) | |
| *A61L 27/18* | (2006.01) | |

(52) U.S. Cl.
CPC ............... *A61K 9/06* (2013.01); *A61K 45/06* (2013.01); *A61K 47/08* (2013.01); *A61K 47/34* (2013.01)

(58) Field of Classification Search
None
See application file for complete search history.

(56) References Cited

U.S. PATENT DOCUMENTS

| | | |
|---|---|---|
| 4,762,129 A | 8/1988 | Bonzel |
| 5,410,016 A | 4/1995 | Hubbell et al. |
| 6,152,943 A | 11/2000 | Sawhney |
| 7,332,566 B2 | 2/2008 | Pathak et al. |

(Continued)

FOREIGN PATENT DOCUMENTS

| | | |
|---|---|---|
| BR | 112014022821 B1 | 3/2021 |
| ES | 2729787 T3 | 11/2019 |

(Continued)

OTHER PUBLICATIONS

Brachi et al., "Intratumoral Injection of Hydrogel-Embedded Nanoparticles Enhances Retention in Glioblastoma", Nanoscale, vol. 12(46), pp. 23838-23850, (Dec. 14, 2020).

(Continued)

*Primary Examiner* — Brian Gulledge
(74) *Attorney, Agent, or Firm* — Peter S. Dardi; Diane E. Bennett

(57) ABSTRACT

Compositions, methods, and applications for single component systems for the formation of in situ hydrogels are described. The single component systems are effective for forming stable, single solutions containing precursors providing both electrophilic and nucleophilic groups that chemically crosslink on contact with physiological fluids associated with vital physiological tissue. The single component systems can be applied using various delivery vehicles, including injections, needle and needless catheters, and sprays. The single component systems can be useful for enabling multiple injections from a single syringe through a small gauge needle or other dispenser. Methods for transcervical installation of in situ formed hydrogels into one or more fallopian tubes are described.

40 Claims, 4 Drawing Sheets

(56) References Cited

U.S. PATENT DOCUMENTS

| | | |
|---|---|---|
| 8,383,161 B2 | 2/2013 | Campbell et al. |
| 8,431,114 B2 | 4/2013 | Kodokian et al. |
| 8,591,929 B2 | 11/2013 | Bennett et al. |
| 9,416,228 B2 | 8/2016 | Bender et al. |
| 9,770,527 B2 | 9/2017 | Hoogenboom et al. |
| 9,868,822 B2 | 1/2018 | Bender et al. |
| 10,925,996 B2 | 2/2021 | Hoogenboom et al. |
| 11,369,591 B2 | 6/2022 | Jarrett et al. |
| 2009/0069226 A1 | 3/2009 | Ong et al. |
| 2011/0251699 A1 | 10/2011 | Ladet |
| 2013/0071462 A1 | 3/2013 | Jarrett et al. |
| 2013/0345319 A1 | 12/2013 | Messersmith et al. |
| 2016/0166504 A1 | 6/2016 | Jarrett et al. |
| 2016/0331738 A1 | 11/2016 | Jarrett et al. |
| 2017/0304453 A1* | 10/2017 | O'Shea .................. A61K 47/34 |
| 2019/0231923 A1 | 8/2019 | Hoogenboom et al. |
| 2019/0290804 A1* | 9/2019 | Askari ................. A61K 9/0024 |
| 2021/0386987 A1 | 12/2021 | Azdoud et al. |
| 2021/0386988 A1 | 12/2021 | Kim et al. |
| 2022/0142653 A1 | 5/2022 | Bassett et al. |
| 2022/0143276 A1 | 5/2022 | Bassett et al. |

FOREIGN PATENT DOCUMENTS

| | | |
|---|---|---|
| WO | 2021018922 A1 | 2/2021 |
| WO | 2021101983 A1 | 5/2021 |

OTHER PUBLICATIONS

Yi et al., "Pharmacokinetic Properties and Antitumor Efficacy of the 5-fluorouracil PEG-hydrogel", BMC Cancer, vol. 10:211, p. 1-8 (2010).

Zhang et al., "Locally Injectable Hydrogels for Tumor Immunotherapy," Gels, vol. 7, 224, pp. 1-20, (2021).

International Search Report and Written Opinion from corresponding PCT application No. PCT/US2023/018665, dated Jul. 19, 2023, 9 pages.

* cited by examiner

SINGLE SOLUTION HYDROGELS WITH COVALENT BONDING FORMED IN SITU, COMPOSITION DESIGN AND MEDICAL PROCEDURES USING THE HYDROGELS

FIELD OF USE

Aspects of the invention relate to composition and methods of applying a single component system for the formation of in situ hydrogels. The invention further relates to stable hydrogel solutions that chemically crosslink on contact with physiological fluids and/or tissue.

BACKGROUND OF THE INVENTION

Hydrogels have found significant use for medical applications ranging from drug delivery platforms, adhesion prevention agents, sealants, space fillers, and organ spacers. Hydrogels based on certain chemistries have achieved wide acceptance based on general good tolerance and few adverse side effects. Corresponding approved products are on the market.

Implants that deliver drugs over time in a therapeutically effective dosage are useful in many fields. In the context of drug delivery, hydrogels can provide the ability to engineer release profiles within selected ranges while providing significant reservoir volumes. Advances in this technology allow for the delivery of a wide range of drugs with different solubilities and stabilities. Hydrogel based drug delivery systems provide abilities to engineer controlled drug release suitable for a range of its applications.

Many in situ formed hydrogels use two component systems, so as to activate the in situ hydrogel forming reactions upon mixing. This provides a discrete starting point and can have advantages of allowing the hydrogel formation to be rapid and dependable. However, special delivery catheters, sprayers, and other devices are typically needed for medical use and the two component nature of these systems can make these delivery systems more complex to design, develop, and use. To date, single component systems have not been developed that can give reproducible polymerization of the hydrogel systems in timescales that are convenient and useful in a medical or surgical setting.

SUMMARY OF THE INVENTION

Biocompatible cross-linked polymers, methods for the preparation and use are disclosed in which a single solution system containing precursors providing both electrophilic and nucleophilic groups capable of reacting and crosslinking in-situ for the formation of hydrogels, that are formed in the absence of separate and distinct precursor solutions. The crosslinking reactions may be carried out in situ after deposition of the single mixture, but the solution embodying the system remains a water soluble mixture containing a selected ratio of electrophilic to neutrophilic groups prior to placement in vivo. Applications for such biocompatible hydrogels include, for example, the formation of injectable depots, spatial or dermal fillers and tissue augmentation, bulking and spacing applications, extraluminal stenting of lumens, including vascular or hollow organ. Additional applications may serve primary or secondary controlled drug delivery applications, for particularly difficult access placement not currently possible with bulkier two-part systems with risk to clogging.

Composition, methods and applications for biocompatible, in situ forming hydrogels are provided in the absence of a chemical or physical activator for use in medical device and pharmaceutical applications. The invention is based on electrophilic and nucleophilic species co-dissolved into a single working system, where the electrophilic species is a macromer, such as a polymer, with reactive functional groups suitable to form adducts with appropriate nucleophiles, and the nucleophilic species can be a macromer, such as a polymer, and is in an acid conjugated form capable of depressing pH when in an aqueous solution, which can be nonbuffered, is used. Unlike similar existing covalent crosslinking hydrogel systems known to the art, the composition requires no separate activator or external activation event to work. Previous art surrounding hydrogel single solution systems require the input of energy in the form of radiation or thermal energy to promote crosslinking for in situ hydrogel formation. Dual systems known to the art require mixing of two components, where an activator is used in the form of pH based accelerators or radical initiators for redox reactions. In contrast, the present single solution system does not involve separation of reactive components, external input from activation sources, or immediate delivery upon mixing to formation of the in situ depot. Dissolution of the electrophilic species and the nucleophilic acid conjugate species in aqueous solutions remains unreactive until introduction into the body, where diffusional exchange of liquid results in neutralization of the acid conjugate species results in elevated local pH at the site of the precursors, with in situ gel formation ensuing. The single solution system may contain therapeutics to provide additional therapy in conjunction with the hydrogel's medical device application, or serve alone as a pharmaceutical depot capable of localized and/or some systemic drug delivery. Therapeutics may be included as low solubility slow eluting components or in suspended drug delivery particles that become further encapsulated by the hydrogel. In some embodiments, the secondary encapsulation by the hydrogel may be using the same or different type of hydrogel, resulting in a suspension of hydrogel particles within the single solution system in situ forming hydrogel formulation.

Methods of application of an in situ forming system derived from a single solution of both electrophilic species and nucleophilic acid conjugated species include introduction through conventional means employing intralumenal delivery. Suitable delivery instrumentalities include injections, needle and needleless catheters, sprayers, and the like, and these devices include tools known to the art. Advantages to the invention include the removal of need for mixing and specialized delivery systems, as well as allowing for multiple injections to be made from the same working system without severe time constraints. Unlike dual reservoir systems known to the art, the system may be stopped and restarted through intralumenal delivery without clogging of the delivery device until desired application is achieved or the system is depleted. The methods of application for single system in situ hydrogel devoid of external activator provide the capability of integration with conventional delivery systems, while removing complications in both dexterity, usability, and access found with previous art.

Applications of a single solution system containing two reactive precursors capable of forming a gel with no external or no secondary activator required for the formation of a depot in the body are ideal in clinical applications where flow of the precursor(s) solution may be restricted, or area of spread may be finite as defined by surrounding tissue/organs/anatomical features. Particularly suitable applications for the inventive compositions involve procedures where gel times can be extended and the need for rapid gelation, such as less than 20 seconds, is not critical and the system is not subject to significant dilution. These uses may include bulk augmentation, such as dermal fillers or ocular injections for scleral bulking or placement of depots into the fornix of the eye. Additional clinical uses may include reinforcement intraluminal walls surrounding hollow vessels and/or organs, to prevent stenosing and occlusion of a lumen. In other applications, the lumen may be opened with a standard balloon catheter, and the single system injected into the wall, accomplished without use of an external activator or specialized catheter delivery equipment. This approach to the opening of lumen could be useful, for example in treatment of benign prostatic hypertrophy (BPH) where the narrowing of the urethral lumen can lead to restriction of urine flow. Injection of the single component hydrogel forming precursor can be done into the body of the prostate, followed by inflation of an intraluminal balloon to mold the urethra in an open expanded position as the precursor solidifies within the prostate and "sets" it in the compressed configuration. The injections within the prostate can be done from within the urethral lumen or also from a transrectal route, similar to that done at the time of prostatic biopsy.

Other applications may include the single solution system being a therapeutic delivery depot, as in the case of fornix inserts, intraocular injections to anterior posterior spaces, and intratumoral injections of chemotherapeutic delivery depots where access is difficult or impossible using conventional catheter access. Multi-pronged needles that allow for a circumferential injection within tumors or even around lumens are useful delivery systems for such precursors. Other applications may be focused on therapeutics where off target drug application has side effects where the ability to make small repeated injections (i.e. tattooing, Botox® injections, or eyelash line injections) can be accomplished with a start stop hydrogel system. Applications for tattooing can provide for tattoos that last for a significant, but limited period of time or with non-degradable hydrogels. Other stop start applications may include multiple needle injections that use a prepared single solution for administration to multiple patients. Other stop start applications unique to a single solution system with acid conjugate that cannot be achieved with two part systems requiring external application include nasal applications, such as sprays, where both nasal cavities require exposure without clogging, or high-pressure needleless injection where crosslinking initiation prior to entering the body would prevent dermal penetration.

One particularly desirable application is directed to the filling of fallopian tube of a patient for birth control or other medical purposes. The hydrogel systems described herein are suitable to have good penetration into the complex structure of the walls of the fallopian tubes. The hydrogels can be designed to persist for long periods of time such as at least about 180 days or perhaps the lifetime of the patient, or for selected shorter periods of time.

In a one aspect, the invention pertains to a medical hydrogel precursor solution comprising a mixture of an aqueous solvent at a pH of no more than about 6, a first precursor comprising a plurality of electrophilic functional groups and a first hydrophilic core, and a second precursor comprising a plurality of protonated amine groups. Generally, the precursor solution is flowable for at least 10 minutes after formation and gels within 20 minutes after dilution with a ⅓ volume of 37° C. phosphate buffered saline (PBS) (3 volumes of hydrogel precursor solution with 1 volume of PBS).

In a further aspect, the invention pertains to a medical hydrogel precursor solution comprising a mixture of an aqueous solvent at a pH of no more than about 6, a first precursor comprising a plurality of electrophilic functional groups and a first hydrophilic core, and a second precursor comprising a plurality of protonated amine groups and a second hydrophilic core.

In an additional aspect, the invention pertains to a method for the delivery of a medical hydrogel for in situ crosslinking, the method comprising:
blending an electrophilic precursor and a nucleophilic precursor with an aqueous solvent at a pH of no more than about 6 to form a precursor solution with a storage stability against restriction of flowability of at least about 10 minutes at room temperature as determined by the precursor solution being injectable from a 5 ml syringe with a 25 gauge needle; and
delivering a quantity of the precursor solution to a patient wherein the precursor solution contacts physiological fluids associated with vital physiological tissue to induce crosslinking of the hydrogel, wherein the hydrogel gels in vivo in no more than about 5 minutes.

In other aspects, the invention pertains to a method for instilling an in situ crosslinked hydrogel into a patent's fallopian tubes, the method comprising:
sequentially delivering a hydrogel precursor solution with an applicator directly into a first fallopian tube of a patient followed by delivery into a second fallopian tube of the patient, wherein the applicator comprises a reservoir of the hydrogel precursor solution connected to a catheter configured for transcervical placement of the hydrogel precursor within a fallopian tube, and wherein the hydrogel precursor solution comprises mixture of a first compound with a plurality of electrophilic groups, a second compound with a plurality of nucleophilic groups, and an aqueous solvent at a pH of no more than about 6, wherein the hydrogel precursor solution gels in contact with the tissue of the first fallopian in no more than about 3 minutes and gels in contact with the tissue of the second fallopian tube in no more than about 3 minutes.

DETAILED DESCRIPTION OF THE INVENTION

Figure 1:
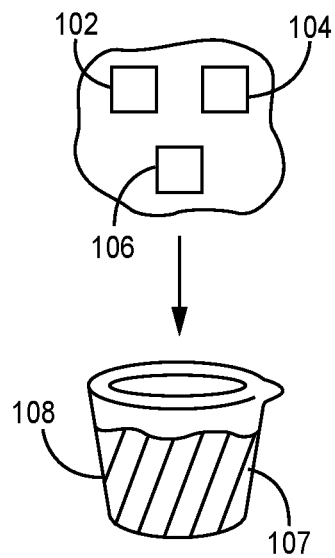
FIG. 1 is an illustration of the preparation of a single solution system.

Medical hydrogels suitable for in situ formation with covalent crosslinking chemistry have been developed for delivery from a single stable solution. Delivery of the hydrogel precursors from a single solution that is stable provides great convenience to a physician for delivery of the composition without necessitating strict planning around time limits set by the precursors stability and for allowing application of hydrogels that were impractical previously. The systems are designed for contact with tissue to effectuate the gelling process through a pH change induced by the natural physiological environment without the application of additional energy sources or initiating solutions. Thus, the processing can be conveniently and efficiently applied without the need for any manipulations other than delivery of the composition. It is advantageous to have single component based formulations that can be delivered by conventional needles and fluid delivery systems that are extensively used already medically. The composition can be effectively used for a range of applications. A particular application suitable for the hydrogel systems described herein involves delivery of hydrogel to fill a woman's fallopian tubes. Other applications include, for example, ocular applications for drug delivery, and drug delivery for tumor treatment, treatment of BPH, delivery of therapeutic drugs around blood vessels, although a range of useful applications are described herein. Various applicator designs can be appropriate, with some of the designs effectively used with one hand.

Two component hydrogel systems have found significant applicability for medical applications involving in situ gelation. Commercial products involving in situ gelation include, for example, DuraSeal® Cranial Sealant (Integra Life Systems), DuraSeal® Exact Spine Sealant (Integra Life Systems), SpaceOAR™ (Boston Scientific), SpaceOAR™ Vue (Boston Scientific) and ReSure® Sealant (Ocular Therapeutix). While the two component hydrogel systems work very well, the precursors are mixed in the catheter during delivery, and the catheters start to clog generally in less than a minute. For some applications, the precursors can be mixed in a vessel for application in a prescribed short period of time, such as less than 20 seconds. For the appropriate applications, these are fine conditions, and the hydrogels can correspondingly gel quickly, in some embodiments in a few seconds or less. For other applications, this timing limitation can be impractical, inconvenient or excessively expensive due to waste of material since the mixed materials need to be used so quickly that remaining material generally cannot be delivered to a second location.

Some hydrogels can be initiated with radiation, such as UV or visible light, to provide for radical imitation of the crosslinking process. See, for example, U.S. Pat. No. 5,410,016 to Hubbell et al., entitled "Photopolymerizable Biodegradable Hydrogels as Tissue Contacting Materials and Controlled-Release Carriers," and WO 2021/101983 to Sheikhi et al., entitled "Tough Tissue Sealants and Use Thereof." both of which are incorporated herein by reference. Embodiments involving UV light delivery, such as with an optical fiber or UV lamp, involve added time to perform the crosslinking by irradiation and expense for the equipment to deliver the UV light or other radiation. For some applications, the use of radiation can be impractical due to timing of the crosslinking as well as the difficulty in directing the radiation to the hydrogel precursors. The electrophile-nucleophile reactions involved in the hydrogels described herein are gated by pH.

To provide for a single applicator delivery of an electrophile-nucleophile mixed precursor system, one effort involved slowing the gelation time sufficiently that the precursors could be mixed immediately prior to use. Such hydrogel embodiments are described in published U.S. patent application 2016/0331738 to Jarrett et al. (hereinafter the '738 application), entitled "Drug Delivery from Hydrogels," incorporated herein by reference. The '738 application teaches buffer added to each of the separate precursors that are then mixed. These hydrogels were specifically designed for eye injections where the hydrogel would not significantly migrate for the gel time, which may be up to 5 minutes, although generally less than a minute. The delivery reservoir would have a comparable pot life as the gel time. These systems would not have the advantages of the hydrogel systems described herein.

A copending application from Applicant describes the mixture of a nucleophilic precursor and an electrophilic precursor that are then mixed and an activator solution during delivery, see U.S. patent application Ser. No. 17/494,752 to Bassett et al. (hereinafter the '752 application), entitled "Transcervical Access Systems For Intrauterine Fluid Exchange, Such As Placement of Hydrogels Formed In Situ," incorporated herein by reference. These systems provided excellent space filing properties under moderate dilution circumstances and provide desirable short gelation times. The further developed alternative hydrogel systems described herein avoid the use of the activation solution and can provide a longer pot-life for deposition of the hydrogels while resulting in somewhat longer gelation times and possibly more sensitivity to dilution effects. Both the present developments in hydrogel systems and the embodiments in the '752 application provide significant functionalities for their corresponding appropriate applications.

A delivery catheter for placement suitable for fallopian tubes are described in U.S. Pat. No. 6,152,943 to Sawhney (hereinafter the '943 patent), entitled "Methods and Apparatus for Intraluminal Deposition of Hydrogels," incorporated herein by reference. While other structures can be used, the basic structure of the catheter in the '943 patent and refinements thereof can be desirable generally for the delivery of hydrogel precursors into fallopian tubes with suitable adaptations for a reservoir of the present precursors. The '943 patent described a two precursor component hydrogel system that are mixed in the catheter during delivery.

A hydrogel is a material comprised of an insoluble hydrophilic polymer that when fully hydrated, is substantially comprised of water in a matrix of the insoluble hydrophilic polymer. Hydrogels may comprise materials that are absorbable or non-absorbable in contact with a patient's bodily fluids, and some hydrogels gradually hydrolyze to break down when in contact with water or other aqueous solution. Some hydrogel systems allow for control of the crosslinking process through delay of crosslinking until hydrogel delivery, e.g., because a large viscosity increase of materials flowing through a delivery device does not occur until after the hydrogel precursor mass is in place. Historically, these systems involve the use of an external activation source that serves a dual purpose. First, it allows injectability of the hydrogel system with activation only after exiting the application device to prevent clogging of the catheter. Second, this allows working time prior to the injection event. In these embodiments, activation generally has been through the use of external radiation such as light to induce radical crosslinking or other energy input for thermally activated polymers, such as thermoreversible polymers or thermally induced radical polymerization. Single systems with external activation sources are unwieldy, limiting certain clinical usage where one handed application or fine dexterity is required, as well as taking longer procedural times. Additionally thermoreversible polymers, which use a single component, do not form hydrogels with mechanical integrity and modulus that is suitable for many medical device and longer persisting drug delivery applications.

In the case of a dual-component system, mixing of the two solutions takes place so that the solutions are fluid while passing through an applicator device and set up to form the hydrogel in situ. Two component systems suffer from the need to mix and the "one and done" approach. These systems typically rely on mixing upon deployment, with pre-mature clogging of the device being a risk for complex placements of the hydrogel or the inability to reapply when multiple or reapplication is desired, such as with two fallopian tubes. For appropriate applications, two component hydrogel systems based on polyethylene glycol hydrophilic cores have found commercial success, such as Duraseal® and Duraseal® Exact (Integra Lifesystems), Mynx® (Cordis), SpaceOAR™ & SpaceOAR VUE™ (Boston Scientific).

Hydrogels described herein can generally be delivered through less invasive means, such as a catheter for in situ gelation. Generally, the hydrogel may begin as a single liquid precursor solution that can form into a gel upon contact with the patient's physiological fluids that enables the formation of the hydrogel by equilibration of the pH with a physiological pH through neutralization of acidified amine groups making them available for crosslinking reactions. The exemplified NHS-amine crosslinking reaction does not occur significantly in unbuffered aqueous systems in the presence of the amine acid conjugate, and similar hydrogel systems follow accordingly. Unreacted co-dissolution may be obtained by forming single solutions with the electrophilic polymer and nucleophilic polymer acid conjugate in unbuffered or weakly acidic buffered solutions that naturally reside at lower pH (generally a pH 2-5). "Pot life" or storage stability is the term that refers to the amount of time that the single solution remains stable after co-dissolution.

The hydrogel precursors describe herein surprisingly have a pot life of at least an hour, but they can gel following delivery to a patient in less than 10 minutes, and in some embodiments less than a minute. As used herein, storage stability refers to the time from mixing hydrogel precursors to form the precursor solution ready for delivery to a patient until a time when the hydrogel is too viscous to a degree that effective delivery is not practical due to effective transition to a non-flowable state. While effective delivery of the precursor solution can depend on the particular application, to specify storage stability of the composition of the precursor solution, this can be evaluated as injectability from a 5 ml syringe through a 24 gauge needle. These hydrogels precursors generally have amines at a pH prior to delivery of no more than 6 pH units and a buffer concentration within tolerances or no added buffer. Dissolved carbon dioxide provides a low amount of carbonic acid, which can be considered a baseline and not an added buffer. Physiological fluids are naturally buffered to account for the overlapping presence of dissolved carbon dioxide, and the presence of dissolved carbon dioxide does not interfere with the performance of the hydrogels. The design of these precursor solutions generally goes against conventional wisdom where a buffer is thought significant for control of the precursor behavior. Through formulation of the precursor solution with a tolerable amount of added buffer or no added buffer, the gel times can be kept desirably low by allowing more rapid equilibration with the patient's physiological pH, generally about 7.1 and 7.6. The low pH of the precursor solution prior to delivery provides for inhibition of significant crosslinking allowing for a significant pot life, which is essentially the time from preparation of the precursor solution until the viscosity becomes high enough to induce clogging of a delivery catheter.

An electrophilic precursor component can have a suitable functional group to crosslink with an amine group to form the hydrogel. The crosslinking functional group is generally pendent on a hydrophilic core, which is generally polymeric, to provide a moderate molecular weight. The precursor generally has three or more crosslinking groups to provide for a highly crosslinked hydrogel. The precursor may or may not have degradable functional groups, which may degrade by hydrolysis. enzymatically or through another biodegradation pathway. The nucleophilic precursor generally comprises three or more amine groups, which generally are pendent on a hydrophilic core. The hydrophilic core of the nucleophilic precursor can be polymeric. The amines in the precursors will generally substantially deprotonate under physiological conditions to render the amines available for crosslinking. The protonated amines are protected from crosslinking by the acidification of the amine, which stabilizes the precursor solution. The ability to rapidly deprotonate under physiological conditions allows for fast crosslinking without a basic buffer.

The single solution system described herein may be used to form a permanent or temporary occlusion in a fallopian tube, such as for the purpose of preventing pregnancy. The single solution hydrogel system overcomes limitations of other methods of pregnancy prevention which are directed to the fallopian tubes. One such method involves the permanent implantation of a metal coil device into the fallopian tubes. After insertion the device plus associated scar tissue would cause occlusion of the fallopian tubes and permanent sterilization. One such device was sold under the brand name of Essure®. Serious side effects have been reported with the Essure® device including headaches, bleeding, allergic reaction, persistent pain, development of a hole in the uterus or fallopian tubes, and movement of the device from the fallopian tubes into the pelvis or abdomen. As reported by the U.S. FDA, sales of Essure® were discontinued in the United States in 2019. Other methods attempted for female sterilization include the formation of a silicone tubal plug by injecting liquid silicon into the fallopian tubes via a hysteroscope. This procedure requires a precise amount of catalyst to be mixed with the liquid silicon in a specific time period before the injection. In practice, the hysteroscope must be carefully placed and aligned prior to the addition of the catalyst. This procedure suffers from high failure rates of plug placement and retention, as well as reactions to the silicone. It is theorized that one aspect of the high failure rates of the silicon plug system is due to the mismatch between the hydrophobic silicone and hydrophilic tissues of the fallopian tubes that does not allow access to the folds and crevices that exist within the fallopian tubes. The silicone in situ plugs underwent clinical trials in the U.S. and have been sold in Europe. Preformed silicone plugs were briefly sold under the tradename Adiana, but sales were discontinued after a few years due to multiple problems. The single solution system herein disclosed is hydrophilic and forms a hydrophilic plug that should be firmly retained. The use of hydrogel polymers with a long history of successful implantation should avoid issues found with other polymer systems.

Anti-tumor drugs can be toxic to normal tissue, so the delivery of anti-tumor drugs can be complicated with respect to delivering desired doses to the tumor without providing toxic levels to surrounding tissue. Improvements in drug treatment have been suggested in trials of the use of hydrogels as a drug delivery matrix in a depot implanted into the tumor. For example, 5-fluorouracil was loaded into a PEG based polymer was tested in mice against induced tumors of human non-small-cell lung adenocarcinoma with promising results. See, Yi et al., "Pharmacokinetic properties and antitumor efficacy of the 5-fluorouracil loaded PEG-hydrogel," BMC Cancer 2010, 10:211, incorporated herein by reference. Similarly, to study avoidance of drug washout in intratumoral drug delivery, a phosphor BODIPY was loaded into microspheres that were then placed into a hydrogel matrix for delivery to tumors associated with of glioblastoma multiforme (GBM), and promising results for drug delivery were observed. See, Brachi et al., "Intratumoral injection of hydrogel-embedded nanoparticles enhances retention in glioblastoma," Nanoscale. 2020 Dec. 14; 12 (46): 23838-23850, incorporated herein by reference. The hydrogel systems described herein are well suited for drug delivery and provide the opportunity for in situ hydrogel formation that can facilitate delivery into the tumor with greater penetration. Extensive experience in drug delivery based on two component hydrogels can be adapted for the present one component systems with the ability to influence drug release profiles.

Hydrogels have been developed to be effective for ocular applications. The hydrogels can provide effective replacement of drops for drug delivery with consistent results. The amounts used generally are small, which can make more routine use for low cost eye drugs prohibitively expensive for two component hydrogels in which the delivery has a very short time window. Using the hydrogel systems described herein for drug delivery, a single batch of prepared drug loaded hydrogel can be used for multiple patients over the pot life of the sample to spread the cost to provide improved and cost effective treatment. A drug loaded hydrogel applied to a patient's eye can spread and coat the eye surface or other target eye location where the hydrogel forms from crosslinking to provide for time released drug to the eye. The hydrogel drug delivery generally can provide more uniform sustained release relative to drop delivery, which can be particularly desirable for certain applications. For example, this can be effectively used after eye surgery as patients complete the procedure, to deliver, for example, steroids, antibiotics, glaucoma drugs, other suitable eye drugs, or combinations thereof. This model can be adapted for other low cost, higher volume situations where the hydrogel systems can provide desirable results. Also, relative to other depots for drug delivery, such as intracanalicular inserts that are pre-formed, in situ single component based depots can be placed through smaller lumens and in generally larger quantities without needing pre-dilatation of the punctal sphincters. These depots can also be placed with fine blunt cannulas into the fornix of the eyes, thus forming larger depots for delivery to the ocular surface. Such delivery systems, by virtue of their larger capacity, allows the use of a wider range of drugs that may be less potent, relative to pre-formed depot formulations.

The hydrogels described herein can be applicable to aesthetic applications, such as dermal fillers for wrinkle removal or the like. Also, the hydrogels with suitable dyes can be used for tattoo formation. The resulting tattoos can be long lasting or designed for resorption and removal at selected time windows. Dyes can be bound to the hydrogels so that the visual effect can last for the same period of time as the hydrogels. The use of dyes, as opposed to pigments of traditional tattoos, provides more flexibility with respect to visual effects. Thus, fluorescent dyes can be especially visible in certain lighting, such as blue, black, or UV light. Generally, vivid images can be formed with images that are not permanent, but can last for significant periods of time, such as months or longer, or potentially shorter periods of time, such as days.

Generally, the in situ hydrogels herein involve at the time of delivery no process of mixing hydrophilic reactive precursor species having nucleophilic functional groups with hydrophilic reactive precursor species having electrophilic functional groups. Instead, reactive precursor species containing an acid conjugate are co dissolved in an aqueous agent with at an appropriate pH such that the acid conjugate of the amine provides sufficient pH depressing activity to limit reaction in the precursor solution. Upon deployment into the body, no mixing with an activator solution (e.g., high pH accelerator) or external activator (e.g., light) is used to promote in situ covalent crosslinking of the gel. In some embodiments, the acid conjugated nucleophilic precursor has a molecular weight not significantly smaller than the molecular weight of the electrophilic precursor and can be the same Mw or larger. In embodiments where small molecular weight amines are used, such as lysine and trilysine, the acid conjugate is generally slow or difficult to deprotonate without mixing of an external accelerator, although for some applications where slower gelling is acceptable, the acid conjugates of these small molecules can be used. The small amine acid conjugates also tend to have a short pot life so this provides another limit on their usefulness.

The hydrogel systems described herein can provide improved delivery for certain applications relative to currently available hydrogels. These hydrogels can be effectively used for space filing, tissue protection, drug delivery and other suitable medical applications. In general, the hydrogels are convenient and readily deliverable.

Hydrogel Systems and Applicators

Generally, at the start of a procedure or series of procedures, an electrophilic precursor and a nucleophilic precursor are mixed with a solvent and placed in a suitable dispenser/applicator, as illustrated in FIG. 1. Various suitable procedures can be used for this formation of the precursor solution, and selection of the process can be based on convenience for the user. If the solvent is combined with the precursors directly in the applicator/dispenser, a step of transfer to the application can be avoided, but the applicator correspondingly then should be suitable for mixing directly in the applicator/dispenser.

To form the solution in the dispenser, electrophilic precursor 102 and nucleophilic precursor 104 are added to dispenser 108. Electrophilic precursor 102 and nucleophilic precursor 104 generally are solids at room temperature, but in principle, at least one precursor can be a room temperature liquid. The two precursors can be provided as a dry powder blend, such that forming a precursor solution involves addition of solvent without a separate precursor blending step. To form a precursor solution, aqueous solvent 106 is added to the precursors in a dispenser 108, and the solution can be mixed until electrophilic precursor 102 and nucleophilic precursor 104 are dissolved. In some embodiments, the separate precursors can be shipped in aqueous solution, but shipping of the precursors free of solvent generally provide convenience, ease of packaging, and simplified sterilization. In some embodiments, dissolution can be determined by the lack of visible particles to the naked eye. Generally, suitable mixing can be performed with shaking by hand. In some embodiments, dissolving occurs in less than 5 seconds, about 5 to 15 seconds, no more than 20 seconds, no more than 30 seconds, no more than 1 minute, no more than 5 minutes, or no more than 15 minutes. A person of ordinary skill in the art will recognize that additional ranges of dissolving times within the explicit ranges above are contemplated and are within the present disclosure. If electrophilic precursor 102 and/or nucleophilic precursor 104 are solid at room temperature, consistent low dissolving times may be obtained by adding the precursor(s) to the dispenser as a powder, such as a fine, flowable powder since high surface area facilitates dissolving. Dispenser 108 may be a syringe for use with the delivering of the single solution system or any other suitable device, such as a dropper for appropriate applications or a catheter with a reservoir. Alternatively, the solution can be mixed in a separate container and drawn into the dispenser, such as drawing the mixed solution into a syringe.

In some embodiments, a syringe barrel may be pre-filled with electrophilic precursor 102 and nucleophilic precursor 104, and aqueous solvent 106 may be drawn into the syringe with a needle or catheter. In further embodiments, a syringe barrel may have a volumetric capacity greater than the volume of solution to provide for sufficient head space for mixing the solution via shaking, swirling, tilting, or the like of the syringe barrel. In some embodiments, the volumetric capacity of the syringe barrel may be from about 1.25 to about 2.5 times the volume of aqueous solvent 106, in further embodiments from about 1.5 to about 2.25 times the volume of the aqueous solvent. A person of ordinary skill in the art will recognize that additional ranges of relative volumes within the explicit volumes above are contemplated and are within the present disclosure.

In other embodiments, aqueous solvent 106 is first added to dispenser 108 and then electrophilic precursor 102 and nucleophilic precursor 104 are added to dispenser 108 and mixed to form the single solution system. For example, the electrophilic precursor 104 and the nucleophilic precursor 106 can be provided as a dry powder blend. Alternatively, a first portion of aqueous solvent 106 is added to electrophilic precursor 102 to form a first precursor solution in a first container and a second portion of aqueous solvent 106 is added to nucleophilic precursor 104 to form a second solution in a second container. The first precursor solution and the second precursor solution may be stored. Prior to use, the first precursor solution and the second precursor solution may be mixed in dispenser 108 to form the single solution system. In general, any reasonable order of mixing can be used to form the solutions for precursor delivery to the patient. In some embodiments, electrophilic precursor 102 and/or nucleophilic precursor 104 are independently a mixture of precursors having different chemical compositions or chemical structure. Differences may include the chemical composition of the core, the molecular weight of the core, the degree of branching of the core, the number of arms, the average molecular weight of arms, the functional groups, the degree of functionalization of the arms, etc. Aqueous solvent 106 is preferably a non-buffered medium.

In some embodiments, aqueous solvent 106 is purified/sterile water (e.g., water for injection), unbuffered saline, or any physiologically acceptable aqueous solution having appropriate buffer capacity. Choice of fluid may be influenced by particular application, although sterile saline for intravenous use (physiological saline) is generally readily available to medical practitioners and safe for most or all uses. In particular, intravenous sterile saline generally is about 0.9 percent weight per volume NaCl or equivalently expressed as 9.0 g NaCl per liter. Effects of buffers can be complicated and depend on both the pKa and concentration. Also, many suitable physiological buffers can be polyprotic, which further complicated their effects. Buffer issues are discussed further below, but for most application more desirable results can be achieved with no added buffer. The precursor solution generally has a polymer solids content of no more than about 30 weight percent, in further embodiments no more than about 27 wt %, in additional embodiments from about 1 wt % to about 25 wt %, and in other embodiments from about 2.5 wt % to about 23 wt %, and in some embodiments from about 5 wt % to about 22 wr %. The polymer solid content can be considered the weigh determined from the added components. A polymer solid content too low can result in undesirable dilution effects that can slow gelling, and a polymer solid content that is too high can result in slow gelling due to slower deprotonation of the amines. The characteristics of the precursors can also influence the selection of the polymer solid content values. A person of ordinary skill in the art will recognize that additional ranges of polymer solid content within the explicit ranges above are contemplated and are within the present disclosure.

Once the precursors are mixed into a single solution, the time can be noted to provide a window for target delivery of the hydrogel prior to the precursor batch expiring. The time window is related to the storage stability, although practical considerations can dictate setting the time window somewhat shorter than the storage stability to provide an extra margin of safety if the time window is not strictly followed. During this time window, one or multiple hydrogel delivery procedures can take place. The practical time window can also be influenced by the mode of delivery for the particular application.

Storage stability can be evaluated in vitro as a property of the precursor solution. Specifically, the storage stability can be the time over which the precursor solution is deliverable using the prescribed delivery approach for the application, while simultaneously gelling after delivery into a physiological solution in an acceptable time unless specifically indicated otherwise. In some embodiments, it may be expected that some crosslinking would occur prior to end of the storage stability time period, but significantly less crosslinking than occurs at gelation. In some embodiments, some hydrolysis can take place prior to delivery, and hydrolysis of the electrophilic ester can take place during storage, and since hydrolysis removes crosslinking groups, the gel time following delivery can be observed to lengthen. Generally, the storage stability is at least about 10 minutes, in other embodiments at least about 15 minutes, in additional embodiments from about 20 minutes to about 2 days, in some embodiments from about 30 minutes to about 10 hours, in further embodiments form about 45 minutes to about 8 hours and in other embodiments form about 1 hour to about 6 hours. Another time parameter is the gel time, which is the time over which the precursors crosslink sufficiently to no longer flow, for convenience, gel time can be measured in vitro. Complete crosslinking can take significantly longer, but once gelation occurs, the hydrogel is generally secured in it deposit location. Gel times are generally desired to be short. In some embodiments, the gel time is no more than 10 minutes, in further embodiments no more than 5 minutes, in additional embodiments, no more than 3 minute, in some embodiments no more than about 2 minutes, in other embodiments from about 2 seconds to about 90 seconds, and in further embodiments from about 10 seconds to about 60 seconds, although in general, the upper cutoff can be selected for a specific application, such as 5 seconds or 10 seconds to 20 seconds, 30 seconds, 40 seconds, 50 seconds, 60 seconds, 70 seconds, 80 seconds, 90 seconds, 100 seconds, or 110 seconds. The gel time is measured in vitro by injecting a volume of the precursor solution at room temperature into a ⅓ volume of phosphate buffered saline (PBS) at 37° C., maintaining the combined volumes at 37° C., and recording the time until a solid or a semi-solid mass is formed, wherein the volume of the precursor solution and the volume of PBS are equal. In other words a volume of precursor solution is injected (combined) with a ⅓ volume of PBS relative to precursor solution. PBS is standard PBS with a pH of about 7.4, which for the purpose of clarity is considered to have 1.37 millimolar (mM) NaCl, 2.7 mM KCl, 10 (8) mM $Na_2HPO_4$, 1.8 (2.0) mM $KH_2PO_4$. A person of ordinary skill in the art will recognize that additional ranges of gel times and storage stability time within the explicit ranges above are contemplated and are within the present disclosure.

With respect to buffers, the hydrogel precursors are not considered to be buffers whether or not they alter the pH and may, in principle, provide some buffer function. In general, dissolved carbon dioxide is present, and this is not considered an added buffer and observations are that carbon dioxide functions as a baseline. The amine precursors are provided in an acidified form with the acidic proton functioning as a protecting group blocking crosslinking. Of course, the acidification is in equilibrium in solution. Upon contact with a bodily fluid at physiological pH, the acidified amine can be neutralized so that it can crosslink at an appropriate rate with the electrophilic precursor. The precursor solution generally should have no added buffer capacity or an appropriate buffer capacity. A buffer can be considered as any Brønsted base, which generally would be an anion ($B^-$) corresponding to a weak acid (HB), in equilibrium with the corresponding weak acid. Anions corresponding to strong acids, such as halide anions, do not act as buffers. If the precursor solution has added buffer capacity, it can shorten the pot life and/or lengthen the gelation time, but such effects can be within tolerable ranges. Effects of buffers depend on the pKa and the concentration. While it is generally desirable have no added buffer apart from impurities and a dissolved carbon dioxide contribution in the precursor solution, appropriate concentrations of appropriate added buffer would generally be acceptable for at least some applications. Due to these complexities, a suitable buffer and concentration can be evaluated based on storage stability and gel times. For many applications, a storage stability of at least about 10 minutes and a gel time of no more than 2 minutes provides a reasonable window on buffer evaluation, although other limits within the general discussion of these parameters can be used as appropriate.

There are various procedures that can benefit from the use of the single solution system described herein. Generally, the single solution systems are particularly useful for delivery into locations where placement requires some period of time to allow for proper placement, such as those where existing two component hydrogels may clog the applicator/dispenser prior to completion of delivery, or where multiple delivery locations involve periods of time for complete delivery that is not suitable with a two component system without using multiple applicators, or where multiple deliveries involve periods of time for delivery of a prepared aliquot of the single solution system to multiple patients. Specific applications discussed below include fallopian tube ligation and drug delivery. For fallopian tube applications, the syringe of FIG. 2 can be attached to an appropriate catheter, as described below. With respect to drug delivery, specific applications may be directed to antitumor drugs or ophthalmic applications. For antitumor drug placement, proper placement may involve significant periods of time, and for ophthalmic drug delivery, a single applicator/dispenser can be used for multiple patients in appropriate settings, with proper accounting for sterilizing or discarding components necessary between patents.

Figure 2:
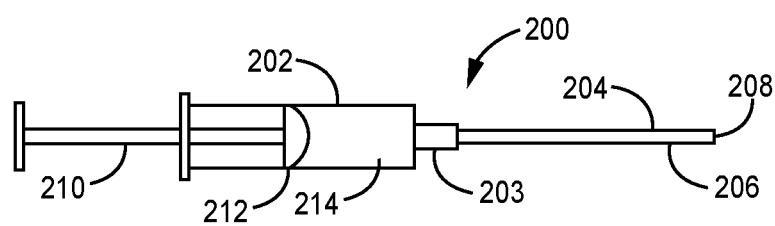
FIG. 2 is a depiction of an applicator with a single reservoir for the delivery of a single solution system.

FIG. 2 displays a dispenser suitable for delivering the single solution system described herein. In this embodiment, dispenser 200 comprises a syringe 202 having connector 203, such as a standard luer lock fitting. A connector 203 connects to a conduit 204 which has a distal end 206 and a delivery tip 208. Basic dispenser 200 also has a plunger 210 which is attached to a plunger seal 212. Plunger seal 212 contacts solution 214 within syringe 202. Delivery of solution 214 through delivery tip 208 may be controlled by pressing plunger 210 In some embodiments, conduit 204 may be a needle or a catheter. In some embodiments, delivery tip 208 has one or more side ports, an open-ended distal port, or a combination thereof. Dispensers for use with the single solution system are not particularly limited and include commercially available applicators. In some embodiments, applicators designed for more complex systems, such as dual solution systems, can be used if desired.

The applicator of FIG. 2 can be effectively used for a range of applications. Conduit 204 can be a generic catheter or needle or can be specifically engineered to facilitate a particular procedure. A specific conduit for delivery to a fallopian tube or similar lumen within a patient is described next. The applicator for the hydrogel precursor can have alternative designs that may be more suited to a particular application whether or not the dispenser of FIG. 2 can be used.

Within the basic formulation of the precursor solution, the nucleophilic precursor and the electrophilic precursor provide the crosslinking functional groups, hydrophilic cores to provide the general hydrogel characteristics and optionally additional functional groups that provide for degradation of the hydrogel following delivery. The details of the precursors control the specific properties of the resulting hydrogels, the delivery of which is controlled by the basic features of the delivery systems as specified in this section. For some applications, it can be desirable to have hydrogels that degrade in appropriate periods of time, and the functional groups can be selected to adjust with some granularity the degradation times, such as using appropriately selected hydrolysable functional groups. In other applications, it can be desirable to use more permanent hydrogels that may only degrade slowly or not at all. These long-lasting hydrogels can be desirable for delivery into fallopian tubes. Additional details of the precursors are provided in the following.

Hydrogel Systems With Chemical Crosslinking

The hydrogel systems described herein to provide desirable medical functions are provided in a single solution that are formulated to provide desired precursor solutions over a time window. The hydrogel precursors can be designed to spontaneously crosslink based on a nucleophilic-electrophilic reaction upon contact with physiological solutions, such as lymph fluid, blood, tissue, other bodily fluids or the like, or similar aqueous solutions. Through the appropriate design of the hydrogel systems, the precursors can be designed so that the precursors are combined into one solution that is stable for a desired amount of time to complete a procedure or a series of procedures, while allowing for rapid crosslinking upon delivery.

Thus, a first aspect of the design of the polymer system is the formation of an appropriately stable initial blend of the precursors. While the polymer precursors should be appropriately stable to not significantly crosslink prior to delivery, the solution should result in reasonably rapid crosslinking upon contact with physiological conditions. The basic chemical structures of the hydrogels and precursors are described next in the context of their properties, and the hydrogel properties are described in more detail below.

The precursors generally comprise at least two different polymerizable compounds, as noted above, but a precursor solution could comprise more than one electrophilic precursor and/or more than one amine precursor. To form highly crosslinked hydrogels, the precursors generally each have more than two reactive functional groups for forming crosslinks. In some embodiments, each precursor compound generally has moderate molecular weights and may comprise polymer moieties. Water soluble polymerizable monomers having a functionality >2 (i.e., that form crosslinked networks on polymerization) and that form hydrogels may be referred to herein as macromers if they possess at least moderate molecular weights and/or polymeric moieties in their core. Molecular weight ranges are discussed further below. The functional groups of the precursors provide for the crosslinking reactions, and the biodegradable feature, if present, as well as the overall properties of the precursor solutions and the product hydrogel.

Generally, pH is used to gate the crosslinking reaction. Thus, the avoidance of added buffer in the precursor solution allows for more rapid pH adjustment upon contact with fluids having a physiological pH can increase the pH to allow for the crosslinking reactions to proceed, generally at a rapid rate, even though no accelerator solution is used. Some appropriately selected buffer can be added to the solution with some increase in gel times that may be acceptable in certain circumstances, and in some embodiments, possible desirable, such as dermal fillers that may be repositioned after delivery prior to gelling. In any case, the contact with the liquid at a physiological pH results in an increase of the pH from the precursor solution that deprotonates the amine groups to provide for advance of the crosslinking reactions. Diffusion resulting in equilibration of pH can occur rapidly for the precursors solutions, and due to the mixture of the precursor molecules, longer distance macromolecular diffusion may not be needed to form highly crosslinked hydrogels. The amine precursors are selected to substantially deprotonate at physiological pH, and the macromer precursors described herein provide this feature. After passing the gel time, further crosslinking occurs over an additional period of time.

In hydrogel systems, suitable functional groups for crosslinking macromers to form tissue implants in situ also may be advantageously used, including macromers that contain electrophilic groups that demonstrate activity toward amine functional groups. Thus, multi-component hydrogel systems can spontaneously crosslink when the components are activated by contact with physiological liquids, but the two or more components are appropriately stable for a reasonable process time before activation by the physiological liquids. Such systems include, for example, monomers (such as macromers) that are di or multifunctional amines in one component and macromers with di or multifunctional electrophilic groups, such as N-succinimidyl containing moieties, in the other component. Succinimidyl functional groups facilitate amide bond formation in reactions with amines and have been used in other medical hydrogels, although other suitable electrophilic precursors are described below.

The hydrogel precursors can have crosslinking activated by the physiological fluids contacted by the precursors following delivery. The hydrogel precursors described herein can be designed to be dilution resistant if formed with a sufficient solids content. Hydrogel and precursor solution properties are described further below. The parameters that influence the properties include: functional group chemistry, crosslinking density/molecular weights of the monomers, monomer composition, percent solids in the hydrogel precursors, and ionic strength.

The crosslinking density of the resultant biocompatible crosslinked polymer is controlled by the overall molecular weight of the macromers and the number of functional groups available per molecule. A lower molecular weight between crosslinks such as 600 will give much higher crosslinking density as compared to a higher molecular weight such as 10,000. Higher molecular weight macromers provide desirable gelation times, and in some embodiments more than 3000 Da, so as to obtain elastic gels. In certain embodiments, the nucleophilic acid conjugated polymer is not significantly smaller in molecular weight than the electrophilic one. In some embodiments, it is the same size or larger.

The crosslinking density also may be controlled by the overall percent solids of the crosslinker and functional polymer solutions. In two component hydrogel systems, increasing the percent solids in the formulation of the precursors, increases the probability that an electrophilic functional group will combine with a nucleophilic functional group prior to inactivation by hydrolysis. Surprisingly, some embodiments of the single solution systems show different behavior. In particular, it has been observed that higher percent solids may be inversely related to the probability of reaction of the electrophilic functional groups with the nucleophilic function groups, perhaps due to slow deprotonation of the amines, although there is no desire to be limited by theory. A single solution system with 25-30% solids can have a significantly longer gel times than a single solution system with 10-15% solids. Ranges of solids concentration are presented above in the discussion of the precursors solutions. While not wanting to be limited by theory, it is thought that the longer gel times are related to slower diffusion of physiological fluids into and/or slower diffusion of the acid conjugate species out of in situ placed solutions having higher percent solids. Yet another method to control crosslink density is by adjusting the stoichiometry of nucleophilic functional groups to electrophilic functional groups. A one to one ratio leads to the highest crosslink density.

Monomers

Monomers capable of being crosslinked to form a biocompatible implant may be used. As noted above, monomers can be macromers, which may or may not be polymers. The term polymer, as used herein, means a molecule formed of at least three repeating groups. Generally, the term "reactive precursor species" means a polymer, functional polymer, macromolecule, or small molecule that can take part in a reaction to form a network of crosslinked molecules, e.g., a hydrogel. As noted above, for the formation of stable one component hydrogel precursor systems, the monomers are generally macromers, as specified below.

Monomers may include, for example, the biodegradable, water-soluble macromers described in U.S. Pat. No. 7,332, 566 to Pathak et al. (hereinafter the '566 patent), entitled "Biocompatible Crosslinked Polymers With Visualization Agents," incorporated herein by reference. These monomers are characterized by having at least two polymerizable groups, and may or may not be separated by at least one degradable region. When polymerized in aqueous solution, they form coherent gels that persist indefinitely or until eliminated by bio-degradation. Generally, a macromer is formed with a core of a polymer that is water soluble and biocompatible, such as a polyalkylene oxide, e.g. polyethylene glycol, which can be flanked by hydroxy-carboxylic acids such as lactic acid, to form degradable esters or non-degradable amides. Suitable monomers, in addition to being biocompatible, and non-toxic, also can be at least somewhat elastic after crosslinking or curing, and in some embodiments are degradable. For the electrophilic compounds or compounds with amine groups, the cores of the compounds can have a plurality of arms or branches each with a functional group suitable for crosslinking. As noted above polyethylene glycol (PEG) based monomers are established hydrogel precursors, and precursor compounds are commercially available.

The nucleophilic functional groups generally are amine groups. The amine groups can be protonated as a protecting group or gate to control crosslinking. The nucleophilic amine groups of the precursors can be designed to significantly deprotonate at physiological pH values, such as from about 7.1 to about 7.6 pH units, although blood and tissue generally is at a narrower pH range in a healthy individual. In some embodiments, the polymers may have a hydrolytically biodegradable portion or linkage, for example an ester, carbonate, or other suitable linkage. Several such linkages are known in the art and originate from alpha-hydroxy acids, their cyclic dimmers, or other chemical species used to synthesize biodegradable articles, such as, glycolide, dl-lactide, l-lactide, caprolactone, dioxanone, trimethylene carbonate or a copolymer thereof.

Generally, the monomer providing electrophilic functional groups and the monomer providing the amine groups are macromers. The macromers generally have biologically inert and water soluble cores with pendent reactive functional groups for crosslinking. When the core is a polymeric region that is water soluble, polymers that may be used can be natural or synthetic polymers. Suitable polymers for the core can include polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, poloxamers, such as Pluronic® F-127; as well as polyvinyl alcohol ("PVA"); poly (vinyl pyrrolidinone) ("PVP"); polylactic acid ("PLA"); and polysaccharides, such as hyaluronic acid, chitosan, dextran or cellulose and derivatives thereof. Based on extensive experience in existing medical products, polyethers and more particularly polyethylene glycol (also known as poly (oxyalkylenes) or poly(ethylene glycol)) are especially suitable.

Smaller molecular weight polyamines have been successfully used in two component polyethylene glycol based hydrogels for medical application. In particular, trilysine has been used. As seen in the examples below, trilysine can be used in a one solution format, but the potlife is lower and the gel times are higher. Nevertheless, for some embodiments, these embodiments may be useful, especially in buffer free systems. Specific small molecule amines include, for example, lysine, dilysine, trilysine, tetralysine, pentalysine, and mixtures thereof. Smaller molecular weight polyamines can have molecular weights generally from 200 to about 1800, in further embodiments, from about 225 to about 1650, and in additional embodiments form about 250 to about 1500. A person of ordinary skill in the art will recognize that additional ranges of molecular weights for lower molecular weight polyamines within the explicit ranges above are contemplated and are within the present disclosure.

It has been determined that hydrogels formed with macromers with longer distances between crosslinks are generally softer, more compliant, and more elastic. Thus, in the polymers of the '566 patent, increased length of the water-soluble segment, such as polyethylene glycol, tends to enhance elasticity. Molecular weights of hydrophilic macromers as used herein, such as macromers with polyethylene glycol macromer cores, generally are at least about 2,000, in some embodiments from about 5,000 to about 500,000, in further embodiments from about 7500 to about 100,000, in additional embodiments from about 10,000 to about 50,000, and in other embodiments in the range of about 15,000 to about 40,000. As used herein, molecular weights (mass) are in conventional units, which can be equivalently Daltons or as a molar mass-grams/mole (assuming natural isotopic presence in either case), and for polymers molecular weights are generally reported as averages if there is any distribution of molecular weights. A person of ordinary skill in the art will recognize that additional ranges within the explicit ranges above are contemplated and are in the present disclosure.

The hydrogel precursors in the hydrogel precursor solutions have a ratio of electrophilic functional groups and amine functional groups. The ratio of functional groups can alter the crosslinking density and the nature of the resulting hydrogel. Generally, if the number ratio of electrophilic functional groups to amines is one to one, the hydrogel can fully crosslink given sufficient time and lack of constraints. Generally, the ratio of electrophilic groups to nucleophilic groups can be from about 0.8 to 1.2, and in further embodiments from about 0.9 to about 1.1, and in further embodiments from about 0.95 to about 1.05, although the ratio can be approximately 1:1. A person of ordinary skill in the art will recognize that additional ranges of ratios within the explicit ranges above are contemplated and are within the present disclosure.

To achieve the desired ratios of functional groups, the functional groups can be distributed in various ways. Pendent functional groups extending form a core can be referred to as being associated with an arm of the precursor. A precursor generally has 2, 3, 4, 5, 6, 7, 8, 9, 10 or more arms. At least one precursor has at least 3 arms to obtain crosslinking, and 4, 6 or 8 armed precursors can be convenient for obtaining desirable hydrogel properties. To obtain a one-to-one ratio of functional groups, equal molar amounts of precursors can be used if they have the same number of arms, or if different numbers of arms are present on the respective precursors, the mole ratios can be correspondingly adjusted. Thus, twice the molar amount of a 4-arm precursor can be combined with an 8-arm precursor to obtain a 1:1 functional group ratio. For weight ratios, the mole ratios can be adjusted accordingly based on the relative weights, for an 8-arm 10K MW (10,000 molecular weight) precursor it would be combined with twice the mass of an 8-arm 20K MW precursor to get a 1:1 functional group ratio. A person of ordinary skill in the art can adjust these calculations to obtain a different number ratio for the functional groups.

Functional Groups and Crosslinking Reactions

The crosslinking reactions generally are designed to occur in aqueous solution in vivo, encircled by physiological conditions, where the hydrogel reaction occurs in a transient local environment. Thus, the crosslinking reactions occur "in situ", meaning they occur at local sites such as on organs or tissues in a living animal or human body. Due to the in situ nature of the reaction, the crosslinking reactions can be designed not to release undesirable amounts of heat of polymerization. Gelation times for desirable procedures are described above, and full crosslinking can be completed generally after times from 15 minutes to 24 hours, although other times outside this range may be acceptable. Certain functional groups, such as alcohols or carboxylic acids, do not normally react with other functional groups, such as amines, under physiologically acceptable pH (e.g., pH 7.2-11.0, 37° C.). However, such functional groups can be made more reactive by using an activating group such as N-hydroxysuccinimide or derivatives thereof. In general, several methods for activating such functional groups are known in the art. Suitable activating groups include, for example, carbonyldiimidazole, sulfonyl chloride, chlorocarbonates, aryl halides, sulfosuccinimidyl esters, N-hydroxysuccinimidyl ester (NHS), succinimidyl ester, succinimidyl amide, epoxide, aldehyde, maleimides, imidoesters and the like. The N-hydroxysuccinimide esters or N-hydroxysulfosuccinimide groups are desirable groups for crosslinking of amine functionalized polymers such as amino terminated polyethylene glycol ("APEG") since they have found acceptance in medical implants from long periods of use in approved products.

Suitable nucleophilic functional groups are polymers with primary amines conjugated to an acid. Thus, the other functional group used for the crosslinking generally is an amine. Amines are weak bases, and the pKa of the protonated amines are dependent on the molecule. In some embodiments, the acid conjugate is HCl and an HCl salted PEG amine is formed. The acid conjugate can be chosen to match the molarity of the amine. The advantage of an NHS-amine reaction is that the reaction kinetics lead to quick gelation usually within 10 about minutes, more usually within about 1 minute and most usually within about 30 seconds. Ultrafast gelation applications with gelation on the order of 5 seconds or less are not generally appropriate for in situ reactions with the precursors described herein. Rather, applications with confined space, such as subdermal or along a surface, generally obtain desirable results.

The protonated amines are generally not suitable for nucleophilic substitution. Thus, the precursor solution can be prepared at a suitable pH to maintain substantially protonated amines prior to delivery for contact with a physiological solution. This preparation can maintain the precursor solutions from prematurely crosslinking.

The crosslinking density of the resultant biocompatible crosslinked hydrogel is controlled by the overall molecular weight of the monomers and the number of functional groups available per molecule. A lower molecular weight between crosslinks such as 2000 Da will give a higher crosslinking density as compared to a higher molecular weight such as 100,000 Da. Higher molecular weight monomers can be used to obtain more elastic hydrogels, and correspondingly lower molecular weight monomers can be used to obtain less elastic hydrogels. Different applications may suggest different properties for the hydrogels.

The crosslinking density also may be controlled to some degree by the overall percent solids of the monomers in the precursor solutions. Increasing the percent solids increases the probability that an electrophilic functional group can combine with a nucleophilic functional group prior to inactivation by hydrolysis. Yet another method to control crosslink density is by adjusting the stoichiometry of nucleophilic functional groups to electrophilic functional groups. A one to one ratio leads to the highest crosslink density. In general, over time, the hydrogel completes curing so that available crosslinking sites form crosslinking bonds. If electrophilic precursor(s) and nucleophilic precursor(s) are provided in equal equivalent amounts it can be expected that approximately all functional groups form crosslinking bonds after full curing. Equal numbers (or reaction equivalents) of the two types agents provides the highest crosslinking density. If a different ratio of functional groups is used, the properties of the cured hydrogel can be accordingly somewhat different. The crosslinking density can depend on the number of functional groups on the precursor molecules as well as the ratio of precursor molecules. A non-stoichiometric ratio of electrophilic and nucleophilic groups can be used to alter the crosslinking density if desired. In some embodiments, the ratio of electrophilic functional groups to nucleophilic functional groups can be from 0.8:1.0 to 1.0:0.8. A person of ordinary skill in the art will recognize that additional ranges within these explicit ranges are contemplated and are within the present disclosure.

Degradable or Non-Degradable Linkages

Depending on the application, it may or may not be desirable for the hydrogel to be degradable, such as through hydrolysis or biodegradation due to enzymatic activity. If it is desired that the biocompatible crosslinked hydrogel polymer be degradable or absorbable, one or more precursors having degradable linkages present in between the functional groups may be used. As used in the art, absorbable polymers can be referred to as biodegradable if they are absorbed under physiological conditions, whether or not they degrade by biological action, such as enzymatic cleavage. The degradable linkage optionally also may serve as part of the water soluble core of one or more of the precursors. In the alternative, or in addition, the functional groups of the precursors may be chosen such that the product of the reaction between them results in a degradable linkage. For each approach, degradable linkages may be chosen such that the resulting degradable biocompatible crosslinked hydrogel polymer degrades or is absorbed in a desired period-of-time range. In other embodiments, functional groups and linkages with functional groups can be selected to resist degradation under physiological conditions to substantially reduce or eliminate degradation.

Generally, degradable linkages are selected that degrade under physiological conditions into non-toxic products. The degradable linkage may be chemically or enzymatically hydrolyzable or absorbable. Illustrative enzymatically hydrolyzable biodegradable linkages include peptidic linkages cleavable by metalloproteinases or collagenases. Additional illustrative biodegradable linkages can be functional groups on the core polymers and copolymers, such as hydroxy-carboxylic acids, orthocarbonates, anhydrides, lactones, (aminoacids, carbonates, phosphonates or combinations thereof. In exemplified embodiments, the degradable linkages are esters formed by hydroxy-carboxylic acid moieties adjacent the electrophilic group used for crosslinking. Esters can degrade gradually by hydrolysis under physiological conditions, with degradation time depending on the specific structure. To have non-degradable hydrogels, the esters formed by hydroxy-carboxylic acid moieties can be replaced by amide groups that generally do not hydrolyze under physiological conditions. Monomers with PEG cores are commercially available with N-succinimidyl electrophilic groups attached with amide linkages or alternatively with ester linkages, for example, from Jenkem Technology, TX, U.S.A. PEG-amines are also available from Jenkem with various numbers of arms and molecular weights. Desirable degradable electrophilic groups with ester linkages include, for example, N-hydroxy succinimidyl succinate (SS), N-hydroxy sulfosuccinimidyl succinate, N-hydroxy sulfosuccinimidyl gluterate, succinimidyl glutarate (SG), succinimidyl adipate (SAP), succinimidyl azelate (SAZ), or a mixture thereof. A correlation is generally found between hydrolysis times and the length of the ester forming group binding to the PEG core. Thus, SS degrades more quickly, other parameters being equal, when in an environment allowing for hydrolysis, such as in vivo. Crosslinking density, monomer sizes and other parameters ca additionally influence degradation times in vivo.

Hydrogel Properties

While not desirable for all applications, the one solution hydrogels described herein can be used for a range of applications. Suitable properties generally are dependent on the particular application. As described in some detail above it is noted that desired degradation times can range from short times such as on the order of a day or less, to intermediate times of several days to several months, and in further embodiments where the hydrogel is non-degradable or degrades over a long time of many years. The flexibility of the chemistry and the experience with similar two component hydrogels allows for similar design of the modulus of the hydrogel, the density, the swelling, and other properties over significant ranges. Measurements of modulus and swelling are described in copending U.S. patent application Ser. No. 17/522,727 to Bassett et a., entitled "Hydrogels Formed In Situ and Composition Design for Intrauterine Use," incorporated herein by reference.

Visualization Agents

Where convenient, the biocompatible crosslinked hydrogel polymer may contain visualization agents to improve their visibility during medical procedures. As used herein, visualization agents can refer to optical visualization (with color), or visualization using an imaging modality, such as x-ray or ultrasound. Visualization agents are especially useful when used in minimally invasive surgery (MIS, e.g., laparoscopy) procedures, due among other reasons to their improved visibility on a color monitor. It is sometimes useful to provide color by adding a colored visualization agent to the single solution system before crosslinking.

Visualization agents (optical) may be selected from among any of the various non-toxic colored substances suitable for use in medical implantable medical devices, such as FD&C BLUE dyes 1, 2, 3 and 6, indocyanine green, or colored dyes normally found in synthetic surgical sutures. In some embodiments, green or blue colors are desirable because these have better visibility in presence of blood or on a pink or white tissue background. While visualization aids are generally applicable to assist with proper placement for medical procedures, visualization agents can also be selected based on aesthetic reasons. Thus, for a tattoo application, the visualization agent can be selected to provide a desired color in the context of forming an aesthetic design.

For dyes used as visualization agents, these are generally water-soluble. Water-soluble dyes can be expected to wash out of the hydrogels relatively quickly. If the dyes have or are modified to have appropriate functional groups, the dyes can be bound to functional groups of the hydrogel precursors, which can be performed prior to crosslinking the hydrogel or simultaneously with crosslinking the hydrogel. Suitable functional groups include for example, amines (—$NH_2$, carboxylates (—$COO^-$), thiols (—SH), or other appropriate electrophilic or nucleophilic groups. Carboxylates can be reacted to form-NHS groups similarly to the precursor compounds. With a single functional group, the dye would not crosslink, but with covalent bonding, the dye would be expected to persist until the hydrogel degrades and is resorbed by the patient. Fluorescein-NHS is commercially available as a fluorescent red/orange dye. A set of dyes can be used for image generation if desired, to cover the primary colors, or alternative colors or shades.

The visualization agent may be present with the precursor solution prior to delivery. The selected colored substance may or may not become chemically bound to the hydrogel. Additional visualization agents may be used, such as fluorescent (e.g., green or yellow fluorescent under visible light) compounds (e.g., fluorescein or eosin), x-ray contrast agents (e.g., iodinated compounds) for visibility under x-ray imaging equipment, ultrasonic contrast agents (e.g., microbubbles), or MRI contrast agents (e.g., Gadolinium containing compounds). Biocompatible visualization agents FD&C BLUE #1 and fluoroscein-NHS can be particularly desirable for some applications. Visualization agents may also be biologically active agents suspended or dissolved within the hydrogel matrix, or the materials used to encapsulate a biologically active agents, if present.

As noted above, visually observable visualization agents can be advantageously used for some embodiments. Wavelengths of light from about 400 to 750 nm are observable to the human as colors (R. K. Hobbie, Intermediate Physics for Medicine and Biology, $2^{nd}$ Ed., pages 371-373). Blue color is perceived when the eye receives light that is predominantly from about 450 to 500 nm in wavelength and green is perceived at about 500 to 570 nm (Id.). Further, since the eye detects red or green or blue, a combination of these colors may be used to simulate any other color merely by causing the eye to receive the proportion of red, green, and blue that is perceived as the desired color by the human eye. The color blue, as used herein, means the color that is perceived by a normal human eye stimulated by a wavelength of about 450 to 500 nm and the color green, as used herein, means the color that is perceived by a normal human eye stimulated by a wavelength of about 500 to 570 nm.

One or more visualization agents can be present in the final electrophilic-nucleophilic precursor solution at a concentration of more than about 0.1 weight percent (wt %) and in some embodiments in a concentration range of at least 0.001 to about 0.075 wt %, and in further embodiments in the range of 0.0025 to 0.05 wt %, although greater concentrations may potentially be used, up to the limit of solubility of the visualization agent and selected concentrations may be influenced by the particular visualization agent and the particular application. In some applications, these concentration ranges were found to give a color to the hydrogel that was desirable without interfering with crosslinking times (as measured by the time for the reactive precursor species to gel). The visualization agent is generally not covalently linked to the hydrogel. A person of ordinary skill in the art will recognize that additional ranges of visualization agent concentrations within the explicit ranges above are contemplated and are within the present disclosure.

In some embodiments, a method is used to form a hydrogel on a tissue until the color of the hydrogel indicates that a predetermined volume of hydrogel has been deposited on the tissue or within the space. The precursors are continually introduced into the space until the color of the materials that enter that space and flow out are deemed to have achieved a suitable content, as indicated by observation of the visualization agent disposed in the materials that flow out.

The visualization agent may serve to help visualize the injection of the hydrogel in specific cases. For example, when injecting into the fornix or subconjunctiva, a visualization agent will help to distinguish the hydrogel from other fluids. Further, the hue of a colored hydrogel may provide information about the concentration of the precursors in the hydrogel or the degree of mixing of physiological fluids into the hydrogel. A dark color hydrogel may indicate a concentration of precursors that is high relative to a lighter hued hydrogel made from the same precursor solutions. The coloring agent may be present in a premixed amount that is already selected for the application. In some embodiments, the dye is conjugated to an electrophilic or nucleophilic end group to allow for incorporation into the depot for visualization with direct correlation to persistence. In some cases, the dye is fluorescence, allowing for visualization under special lighting conditions only and render the single system gel otherwise invisible under normal visual conditions.

In some embodiments, a user can apply a single system hydrogel depot to a tissue location with a selected visualization agent to observe directly the injectable depot. The user may use visualization agents to see the hydrogel with the human eye or with the aid of an imaging device that detects visually observable visualization agents, e.g., a video camera. A visually observable visualization agent is an agent that has a color detectable by a human eye. A characteristic of providing imaging to an X-ray or MRI machine is not a characteristic sufficient to establish function as a visually observable visualization agent. An alternative embodiment is a visualization agent that may not normally be seem by the human eye but is detectable at a different wavelength, e.g., the infrared or ultraviolet, when used in combination with a suitable imaging device, e.g., a video camera. Hydrogels with visualization agents for x-ray and/or ultrasound visualization are described further in U.S. Pat. No. 8,383,161 to Campbell et al., entitled "Radioopaque Covalently Crosslinked Hydrogel Particle Implants," incorporated herein by reference. Ultrasound visualization can be particularly desirable for fallopian tube procedures, and x-ray visualization can be particularly desirable for tumor delivery.

Therapeutic Agent Delivery

Crosslinked hydrogel materials advantageously may be used for localized or systemic therapy with a therapeutic agent, such as a drug. Biologically active agents or drug compounds that may be added and delivered from the crosslinked polymer or gel include: proteins, glycosaminoglycans, carbohydrates, nucleic acid, inorganic and organic biologically active compounds where specific biologically active agents include but are not limited to: enzymes, anti-infectives, antifungals, anti-inflammatories, antineoplastic agents, local anesthetics, hormones, angiogenic agents, anti-angiogenic agents, growth factors, antibodies, a pain reliever, an anesthetic, a steroid, neurotransmitters, psychoactive drugs, anticancer drugs, chemotherapeutic drugs, anti-tumor drug, a glaucoma drug, drugs affecting reproductivity, genes, oligonucleotides a glycosaminoglycan, an antibiotic, a non-steroidal anti-inflammatory drug, an antineoplastic agent, an intraocular pressure-lowering agent, a neurotransmitter, a psychoactive drug, an anticancer drug, cells, a cellular product, or combinations thereof. As used herein, therapeutic agent will refer to any biologically active agent or drug. Various formulations have been developed to provide for effective therapeutic agent delivery from hydrogels with selective release rates.

To prepare such crosslinked composition, the therapeutic agent can be mixed with the crosslinkable polymer precursors prior to, at the time of or following making the aqueous precursor solution. This mixture of precursors and therapeutic agent then can be injected as a single solution system for in situ polymerization at the target delivery site. The biodegradation rate of the polymer may or may not be selected to coordinate with the therapeutic agent elution rate depending on the nature of the therapeutic agent and the hydrogel.

In some embodiments, a therapeutic agent or agents are present in a separate phase when crosslinkable polymers are reacted to produce a crosslinked polymer network or gel. This phase separation can prevent participation of therapeutic agent in the chemical crosslinking reaction, such as reaction between NHS ester and amine group. The separate phase also helps to modulate the release kinetics of active agent from the crosslinked material or gel, where 'separate phase' could be oil (oil-in water emulsion), biodegradable vehicle, and the like. Biodegradable vehicles in which the active agent may be present include: encapsulation vehicles, such as microparticles, microspheres, microbeads, micropellets, and the like, where the active agent is encapsulated in a bioerodable or biodegradable polymers such as polymers and copolymers of: poly(anhydride), poly(hydroxy acid)s, poly(lactone)s, poly(trimethylene carbonate), poly (glycolic acid), poly(lactic acid), poly(glycolic acid)-co-poly(glycolic acid), poly(orthocarbonate), poly(caprolactone), crosslinked biodegradable hydrogel networks like fibrin glue or fibrin sealant, caging and entrapping molecules, like cyclodextrin, molecular sieves and the like. Microspheres made from polymers and copolymers of poly (lactone)s and poly(hydroxy acid) are of particular interest as biodegradable encapsulation vehicles.

In general, the therapeutic agent or encapsulated therapeutic agent may be present in solution or suspended form in in the single solution system. The chemical reaction between the nucleophile and the electrophile readily takes place to form a crosslinked gel and acts as a depot for release of the active agent to the host. Such methods of therapeutic agent delivery may find use in systemic and/or local administration of the therapeutic agent.

In using the crosslinked composition for therapeutic agent delivery as mentioned above, the amount of crosslinkable polymer, crosslinker and the dosage agent introduced in the host appropriately depends upon the particular therapeutic agent and the condition to be treated. Administration for in situ gelation may be by any convenient means, such as syringe, cannula, trocar, catheter and the like. Once the depot is formed, release of a therapeutic may ensue resulting in localized treatment to the area. In some locations, blood flow can result in systemic distribution of the therapeutic agent, or perhaps organ-wide distribution of the therapeutic agent.

Certain embodiments of the therapeutic agent delivery hydrogels are accomplished by providing compositions and methods to control the release of relatively low molecular weight therapeutic species using hydrogels. In accordance with the principles herein, a therapeutic species first is dispersed or dissolved within one or more relatively hydrophobic rate modifying agents to form a mixture. The mixture may be formed into microparticles, which are then entrapped within a bioabsorbable hydrogel matrix so as to release the water soluble therapeutic agents in a controlled fashion. Alternatively, the microparticles may be formed in situ during crosslinking of the hydrogel.

In one method of forming therapeutic agent delivery hydrogels, hydrogel microspheres are formed from polymerizable macromers or monomers by dispersion of a polymerizable phase in a second immiscible phase, wherein the polymerizable phase contains at least one component required to initiate polymerization that leads to crosslinking and the immiscible bulk phase contains another component required to initiate crosslinking, along with a phase transfer agent. Pre-formed microparticles containing the water-soluble therapeutic agent may be dispersed in a hydrogel precursor solution as described above.

Embodiments of the compositions and methods for forming composite hydrogel-based matrices and microspheres can have entrapped therapeutic compounds. In one embodiment, a bioactive agent is entrapped in microparticles having a hydrophobic nature (herein called "hydrophobic microdomains"), to retard leakage of the entrapped agent. In some embodiments, the composite materials that have two phase dispersions, where both phases are absorbable, but are not miscible. For example, the continuous phase may be a hydrophilic network (such as a hydrogel, which may or may not be crosslinked) while the dispersed phase may be hydrophobic (such as an oil, fat, fatty acid, wax, fluorocarbon, or other synthetic or natural water immiscible phase, generically referred to herein as an "oil" or "hydrophobic" phase).

If an oil phase is used, the oil phase entraps the drug and provides a barrier to release by slow partitioning of the drug into the hydrogel. The hydrogel phase in turn protects the oil from digestion by enzymes, such as lipases, and from dissolution by naturally occurring lipids and surfactants. The latter are expected to have only limited penetration into the hydrogel, for example, due to hydrophobicity, molecular weight, conformation, diffusion resistance, etc. In the case of a hydrophobic drug which has limited solubility in the hydrogel matrix, the particulate form of the drug may also serve as the release rate modifying agent.

Hydrophobic microdomains, by themselves, may be degraded or quickly cleared when administered in vivo, making it difficult to achieve prolonged release directly using microdroplets or microparticles containing the entrapped agent in vivo. In accordance with some embodiment, however, the hydrophobic microdomains are sequestered in a gel matrix. The gel matrix protects the hydrophobic microdomains from rapid clearance, but does not impair the ability of the microdroplets or microparticles to release their contents slowly. Visualization agents may be included, for instance, in the gel matrix or the microdomains.

In other aspects of the compositions, the active agent is hydrophobic and poorly water soluble, and itself a hydrophobic domain. The insoluble drug particle may be micronized in nature to allow for homogenous suspension throughout the entirety of the hydrogel and to allow for consistent application without clogging of the delivery system. On formation of the in situ system, the hydrophobic poorly soluble drug particles remain confined within the gel matrix, forming a concentrated environment that acts as a diffusion barrier to further drug dissolution as the drug is required to dissolve and then diffuse out of the matrix for release. Poorly soluble hydrophobic drugs may undergo zero or first order release kinetics as a function of their solubility, the amount loaded into the gel, and the surface area of the hydrogel as applied. In more confined environments such as ocular or subdermal, release kinetics may be further extended as local tissue is saturated with drug, further restricting the diffusion path out of the hydrogel.

In another aspect of the compositions, the hydrogel microspheres are formed having a size that will provide selective deposition of the microspheres, or may linked with ligands that target specific regions or otherwise affect deposition of the microspheres within a patient's body.

Controlled rates of drug delivery also may be obtained with the system of the present invention by degradable, covalent attachment of the bioactive molecules to the crosslinked hydrogel network. The nature of the covalent attachment can be controlled to enable control of the release rate from hours to weeks or longer. By using a composite made from linkages with a range of hydrolysis times, a controlled release profile may be extended for longer durations.

In certain embodiments, the addition of the therapeutic agent does not elevate the existing pH of the unbuffered system such that it overwhelms the acid conjugate. In other embodiments, encapsulation or phase separation of the therapeutic agent. The choice of therapeutic agent is generally influenced by the particular applications. In that context, some specific drugs/therapeutic agents are mentioned in the following discussion of specific applications.

Fallopian Tube Occlusion

Hydrogels can provide desirable functionality with respect to occluding fallopian tubes as a means of birth control or other medical reasons. The one solution hydrogel systems described herein are particularly convenient due to removal of significant time constraints with respect to delivering hydrogel to both fallopian tubes. The hydrogels can be effective to conform to the irregular surfaces of the fallopian tubes, and the constrained space can be consistent with the fast but somewhat slower gelation times, relative to two component hydrogel systems. A specific applicator is described, although other devices can be used as desired.

Figure 3A:
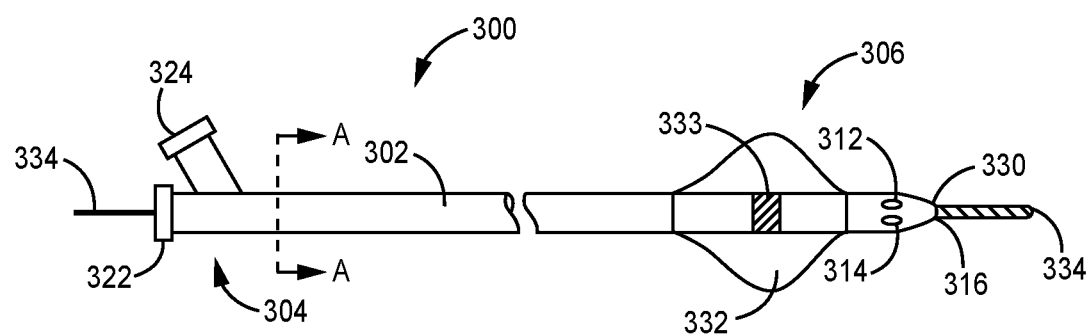
FIG. 3A is a side view of a delivery system for injecting a single solution in situ crosslinkable precursors to occlude a body lumen.
Figure 3B:
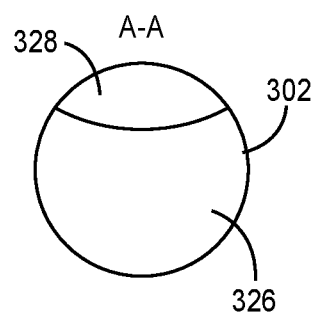
FIG. 3B is a cross-section of FIG. 3A along view line A-A.

FIGS. 3A and 3B display a delivery system applicator suitable for the delivery of the single solution described herein to occlude a body lumen, such as a fallopian tube. Delivery system 300 comprises multi-lumen catheter 302 having proximal end 304 and distal end 306. Proximal end 304 includes inlet port 322 which is coupled via lumen 326 to outlet port 312, 314, 330 disposed near tip 316. Balloon inflation port 324 is coupled via balloon lumen 328 to balloon 332. The two lumen 326, 328 can be seen in the cross sectional view of FIG. 3B. In this embodiment, lumen 326 functions both as a guidewire lumen and a lumen for the delivery of the hydrogel. With guidewire 334 in place, outlet port 330 is substantially blocked for exit of hydrogel precursor solution. Alternatively, in operation, lumen 326 initially may be used to position delivery system 300 in a desired position, and guidewire 334 is then withdrawn. The single solution is then injected through inlet port 322 and into lumen 326, and finally exiting through outlet port 330, and outlet ports 312, 314 may still be used or removed.

Radio-opaque marker band 333 is disposed within balloon 332, or elsewhere on distal end 306, to assist in positioning distal end 306 of delivery system 300 within a body lumen under fluoroscopic guidance. Guidewire 334 extends through inlet port 322 and outlet port 330, and may be used, for example, to intraluminally guide tip 316 of delivery system 300 to a treatment site, such as a fallopian tube, a peripheral blood vessel, aneurysm, or other bodily lumen. Balloon 332 may be inflated to anchor catheter 302 in position within a body lumen during formation of a hydrogel implant, and may also occlude a lumen to prevent fluid flow from diluting the single solution system during gelation. Delivery system 300 optionally may include an outer sheath that surrounds balloon 332 when the balloon is deflated.

Alternatively, catheter 302 may be configured to have three lumens, for example, a hydrogel precursor lumen, a guidewire lumen, and a balloon lumen, thus providing separate guidewire and hydrogel precursor lumens such that outlet port 330 is not coupled to outlet ports 312 and 314. In this case, a hydrogel precursor lumen couples a hydrogel precursor inlet port to outlet ports 312 and 314, a guidewire lumen couples inlet port 322 to outlet port 330, and balloon lumen 328 couples balloon inflation port 324 to the interior of balloon 332. In operation, the guidewire lumen is used to position delivery system 300 in a desired position, and then the single solution is injected through the hydrogel precursor inlet port. The solution crosslinks after placement in the body lumen. As a further alternative to the embodiment of FIGS. 3A and 3B, the guidewire lumen need not extend the length of the catheter to form a so-called "over the wire" catheter. Instead, the guidewire lumen may be configured as a shorter lumen that exits catheter 302 through a skive just proximal of balloon 332 to form a so-called "rapid exchange" catheter, as described, for example, in U.S. Pat. No. 4,762,129 to Bonzel.

Figure 4:
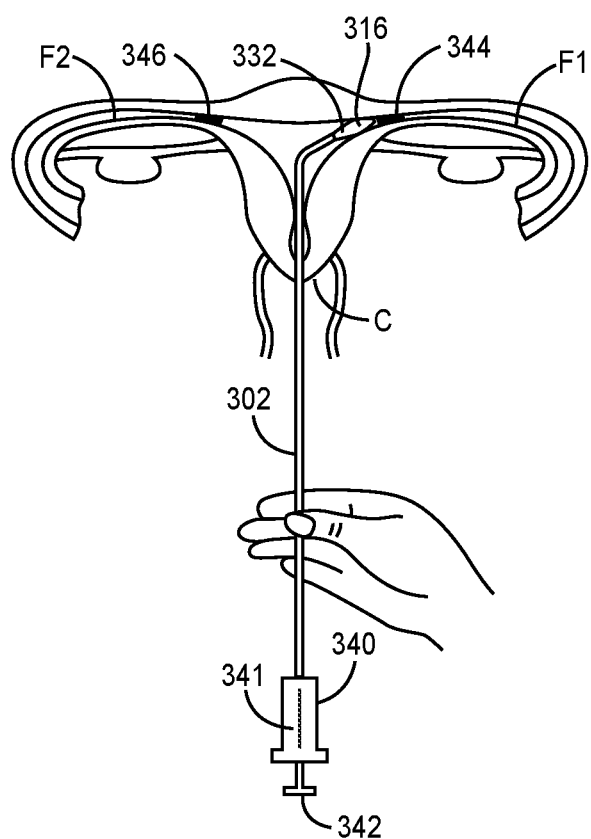
FIG. 4. illustrates a method of using the apparatus of FIG. 3A to occlude fallopian tubes.

Referring to FIG. 4, a method of using delivery system 300 of FIG. 3A is described for delivering the single solution system into fallopian tube lumen to form hydrophilic hydrogel occlusions. Fallopian tube F1 is accessed by passing catheter 302 through cervix C under fluoroscopic guidance. Proximal end 304 of delivery system 300 is coupled to single syringe-type device 340 containing single solution system 341 and having actuator 342 that allows controllable injection of the single solution system 341. Balloon 332 may be inflated with a fluid containing a contrast agent to verify placement of tip 316.

If desired, following inflation of balloon 332, the treatment space may be filled or flushed with a solution, such as an inert saline solution, to remove blood and other physiological fluids from the treatment space. Delivery system 300 optionally may include an additional lumen or use an existing lumen, such as lumen 326, to permit such flushing liquids to exit the treatment space. Alternatively, a non-inert solution, such as a solution containing a pharmaceutical agent, may be injected into the treatment space.

Actuator 342 is then depressed so that single solution system 341 is delivered within the fallopian tube through one or more outlet port distal of balloon 332. The delivery rate and overall delivery time of single solution system 341 is not particularly limited. In some embodiments, the delivery time is about 30 seconds, about 1 minute, about 5 minutes, or about 10 minutes. In some embodiments, an initial delivery of single solution system 341 may be performed with pauses of several seconds or several minutes. The single solution crosslinks with about 30 seconds to about 5 minutes after contact with the fallopian tube tissue, thus forming plug 344 that occludes fallopian tube F1. Balloon 332 is then deflated and catheter 302 partially withdrawn. Continuing to use delivery system 300, fallopian tube F2 is then accessed under fluoroscopic guidance and the procedure above repeated to form plug 346.

In some embodiments, the method of fallopian tube occlusion may be made controllably reversible by using a single solution system 341 that forms plugs 344 and 346 that are degradable after a selected period of time. The choice of the nucleophilic and electrophilic functional groups can be used to tailor the degradation time of the hydrogel plug. In other embodiments, the method of fallopian tube occlusion may be made permanent by using nucleophilic and electrophilic functional groups that react to form linkages, such as amide linkages, that are resistant to hydrolytic degradation. A tubal patency check may be performed immediately after insertion of plugs 344 and 346, at regular intervals, and/or after the selected period of time for reversal to test the effectiveness of plugs 344 and 346 to occlude fallopian tubes F1 and F2.

For these applications, the hydrogels can be loaded with some selected drugs. Suitable drugs can include, for example, anti-infectives or anti-fungals for the treatment of uterine infections, where effectivity of the agent is improved due to its local target proximity. For example, the following antimicrobials can be suitable: anti-viral agents, broad spectrum antibiotics (such as penicillins and cephalosporins), metronidazole (for bacterial vaginosis and trichomonas), fluconazole (anti-fungal—for yeast infection), doxycycline, or azithromycin. Certain cases may call for the anti-infective agent to be deployed prophylactically. Anti-inflammatoires, such as NSAIDs or steroids, are another class of agents that may be used to treat conditions such as endometriosis, without the systemic side effects associated with long-term consumption of these agents.

Agents such as hormones benefit from local intrauterine delivery, ranging from treatment of endometriosis or as hormone replacement therapy (HRT) in post-menopausal women. Oral contraceptive consumption is associated with increased risks in thromboembolisms as well as rates of breast cancer. More benign side effects of oral contraceptive use, such as mood changes, weight gain, intermenstrual vaginal bleeding and spotting, and loss of libido, may lead to inconsistent oral administration or discontinuation, translating into a failure rate for oral contraceptives as high as 5% during the first year of use. On the other end of the life cycle, oral administration of HRT in post menopausal women is associated with an increased risk for coronary heart disease, stroke, and venous thromboembolism, as well as increased risk for breast cancer the longer the treatment lasts.

Anti-Tumor Drug Delivery

The hydrogel systems described herein provide a significant tool in the context of drug delivery to treatment of tumors. The use of the single solution systems described herein provide the advantage of allowing for efficient injection into tumors at multiple locations without clogging of the applicator. Therefore, a more uniform delivery of the anti-tumor agents can be achieved. The tumors can be accessed using appropriate medical techniques for the particular tumor location, as understood by a person of ordinary skill in the art.

The particular medications can be selected based on the particular tumor type, and generally the drug will be approved by the relevant medical regulatory agency. The hydrogel delivery approach can be effective for delivery of drugs that may not have effective delivery approaches using non-targeted approaches, such as systemic delivery approaches, for example, due to toxicity or solubility constraints. Thus, cytotoxins can be delivered with these hydrogel systems, and drug elution rates can be designed accordingly.

The Yi et al. article cited above discusses the hydrogel delivery of anticancer drug 5-fluorouracil, and this drug can be similarly delivered with the single solution, in situ hydrogels described herein. 5-fluorouracil is used generally in the treatment of colorectal cancer, oesophageal cancer, stomach cancer, pancreatic cancer, breast cancer, cervical cancer, actinic keratosis, and basal cell carcinoma. Other classes of anticancer agents include, for example, monoclonal antibodies, cytokines, A review of the use of the potential for hydrogel delivery of anti-cancer agents is found in Zhang et al., "Locally Injectable Hydrogels for Tumor Immunotherapy," Gels, 2021, 7, 224, incorporated herein by reference.

Select Further Embodiments

In some embodiments, the hydrogel may comprise a polymer comprising the group-$(CH_2CH_2O)$—. The hydrogel may further comprise a therapeutic agent. In some embodiments, the hydrogel may be degradable in vivo. For example, the hydrogel may be hydrolytically degradable. The hydrogel may be degradable in vivo in less than 5 days, less than 8 days, less than 15 days, while in other embodiments, the hydrogel may not degrade in vivo. The hydrogel may be degradable in vivo in more than about one half day and in less than about 770 days. In general, the degradation time can be selected appropriately for the particular applications. A person of ordinary skill in the art will recognize that additional ranges of degradation times with in the ranges above are contemplated and are within the present disclosure.

The method of applying the hydrogel can comprise applying a single solution system containing two reactive precursors capable of forming a hydrogel with no external or secondary activator. The method may comprise the application of two or more reactive precursor components in an aqueous system to form an in situ gel in the absence of external activator such as radiation, pH accelerants, redox reactions or thermal activation. The hydrogel precursor solution may be applied through an intraluminal tract, including catheter, needle, port using standard fluid application methodologies associated with single system injections in the absence of a need for mixing. The method of application may incorporate a visualization agent. In some embodiments, the agent is a water soluble biocompatible dye such as FD&C Blue #1 to provide contrast to opposing tissue and/or blood. In other embodiments, the dye may be conjugated to an electrophilic or nucleophilic group and premixed with the reactive precursors in the same single aqueous solution. In specific embodiments, the dye is a fluorescein-NHS conjugate capable of attaching to the hydrogel network and making the gel observable via fluorescence through the tissue.

The use of a single solution system containing two reactive precursors capable of forming a gel can be performed with no external or secondary activator required for the formation of a depot in the body. The use of a single solution system in clinical applications where flow of the precursor(s) solution may be restricted, or area of spread is finite, as defined by surrounding tissue/organs/anatomical features where the need for rapid gelation is not critical. In more specific applications, the gel time may range from 10 s to 10 min, in further embodiments from 15 s to 5 min, and in other embodiments from 20 s to 2 minutes. A desirable feature of the hydrogel systems described herein is that no unique or custom delivery systems are required for delivery of the system, and it may be started and stopped repeatedly through use, although for some applications a specific applicator may be desired. Applications can have, for example, delivery locations suited for the crosslinking to occur after entry into the body without the addition of a secondary activation source such as radiation. Some specific applications include, for example, tattooing or high pressure needless injections, where even small onset of crosslinking initiated prior to passing the dermis would result in significantly reduced penetration efficacy and/or clogging. Other applications are directed to nasal locations, where more than one injection may be desired through the presence of more than one orifice.

In certain applications, the delivered depot may serve as a bulking agent for tissue augmentation. Augmentation may include dermal filling or intraluminal bulking, such as augmentation of hollow vessel or organ walls to prevent stenosis of the intraluminal cavity. Bulking applications may include sphincter augmentation throughout the body, or cervical bulking for the prevention of premature birth. Conversely, use of the single solution system in the presence of an inflated conventional balloon catheter to augment and further open a hollow vessel. This may include the bulking of a urethra in the presence of a swollen prostate to reduce regular catheterization for bladder relief. Augmentation can also have aesthetic application, such as with respect to smoothing or wrinkles and the like. Augmentation can be performed with shorter dwelling or longer dwelling, such as non-degrading, hydrogels. Other aesthetic applications include tattoo application. Traditional tattoos are essentially permanent, which can require painful processing for their removal. The use of dyes for forming the tattoos are described above, and bonding of the dyes to the hydrogel can provide for persistence of the dyes over the persistence time of the hydrogel and removal of the dye with the breakdown of the hydrogel. Temporary tattoo would generally be short duration and have a different look from traditional tattoos. The hydrogel based tattoos can be relatively long lasting, offer the potential for a similar appearance and be medically safe. The compositions can be delivered using medical needles or standard tattoo instruments, i.e., see published U.S. patent applications 2021/0386988 to Kim et al., entitled "Tattoo Needle Unit," and 2021/0386987 to Azdoud et al., entitled "Robotic Tattooing Systems and Related Technologies," both of which are incorporated herein by reference.

In some embodiments, any or all the clinical applications can be suitable where an active therapeutic may be added to provide localized therapy. In some embodiments, the addition of the therapeutic is a complimentary effect to the action of the device, such as addition of anesthetic to bulking injections for the reduction of injection event pain. In others, more traditional therapeutic may be required. Applications using the single precursor solution are distinguished from embodiments using a dual solution precursor system since specialized equipment is not needed and reduced manual dexterity may be involved. Other desirable applications may involve uses where adjustable volume requires finesse and stop start applicability is desirable. One such application would be trans-tympanic applications of therapeutic depots to the ear, where injection without fear of clogging is more effective to prevent unwanted injection event side effects.

In certain embodiments, applications are purely for the formation of a depot for therapeutic release, such as intra-tumor direct injections containing a therapeutic for chemotherapeutic delivery where conventional access including endovascular is not possible. Other embodiments include delivery of chemotherapeutics for treatment of cancers where 4-6 months of therapy are required. Therapeutics delivery may be accomplished through high loading of low solubility compounds, secondary encapsulation or methods known to the art. Therapeutic delivery may also be accomplished through the incorporation of a secondary hydrogel particulate system containing the therapeutic, to be suspended within the primary system.

Other therapeutic clinical embodiments involve ocular surface depot formation, such as ocular fornix based depots for therapeutic delivery including for treatment of infection, allergy, inflammation and glaucoma. Additional embodiments include intraocular injections for sustained release to anterior and/or posterior chambers of the eye, with therapies targeted for delivery of antinflammatories, antiinfectives, biologics, prostaglandins, betablockers, and the like.

Other suitable applications can involve need for minute repeat administration of single system depot where off target application leads to undesirable side effects. An example of such an application would be tattooing with a single system the eyelid margin with a sustained depot of prostaglandin to enhance lash thickness without off target browning of the eye area or potentially the iris. Latisse (Allegan) is an FDA approved product containing prostaglandin bimatoprost that can be applied along the eyelid margin to thicken and otherwise enhance eyelashes. Dual hydrogel precursor systems would require painting the exterior of the lid similar to Latisse to achieve surface area coverage without clogging, leaving hydrogel depot application subject to drying and friability. Other injections include prostaglandin below the eye for sustained ablation of fat and reduction of "baggy eyes", where a single system with acid conjugate and no activator can be spread with multiple injections, and dual systems known to the art would result in undesirable single large bolus injections. XAF5 (developed by Topokine Therapeutics) is a topical ocular ointment containing prostaglandins for use to reduce eye bagginess and is in clinical trials.

EXAMPLES

Example 1: In Vitro Performance Study

This example demonstrates the performance of a single component system via an in vitro model of a reservoir of physiological fluids.

The single component system was prepared by combining a first precursor and a second precursor, both as dry powders, unbuffered water-for-injection (WFI, pH 5.5), and a trace amount of FD&C Blue #1 (less than about 0.011% w/w) to form a solution having a precursor concentration of 10% w/w. The solution was blue in color. The first precursor was an eight-armed polyethylene glycol-based precursor having a 15,000 Da molecular weight and succinimidyl glutarate (SG) functional end groups (8A15k PEG SG, Jenkem USA). The second hydrogel precursor was an eight-armed polyethylene glycol-based precursor having a 20,000 Da molecular weight and HCl-salted amine functional end groups (8A20k PEG amine-HCl, Jenkem USA). The first and second precursor were used in a 3:4 weight ratio in order to provide an approximately equivalent number of SG and amine functional end groups in the solution. The precursors dissolved rapidly in the WFI, as determined by the absence of particulates upon visual inspection. Immediately after dissolution, the prepared solution was drawn into a 5 ml syringe and affixed with a 27G gauge needle. For a period of 30 minutes, occasional 200 µl injections of room temperature solution were made through the 27G gauge needle into 200 µl aliquots of phosphate buffered saline (PBS) at 37° C. The solution remained flowable and injectable through the ** gauge needle for the entire working window observation time frame of 30 minutes. Each injection resulted in the formation of a blue-colored, solid to semi-solid mass in the PBS solution due to crosslinking of the precursors leading to gel formation. This study showed that the single component system has a stability of more than 30 minutes after preparation.

Example 2: In Vitro Performance Study (with Comparative Example)

This example demonstrates the time-dependent performance of the single component system of Example 1 and a single component system having trilysine as the second hydrogel precursor. Comparisons were made to single solution composition that was similar to the system of Example 1, except the amine functional end groups of the second precursor were not HCl-salted.

The two single component systems ("Study System 1" and "Study System 2") and the comparative system (CS-1) were prepared from a first precursor, a second precursor, and unbuffered water-for-injection (WFI), according to Table 1. CS-1 was prepared from same precursors as the Study System 1, with the exception that the second precursor in CS-1 was not HCl-salted. The precursors, in the form of dry powders, were combined with the WFI and a trace amount of FD&C Blue #1 (less than about 0.011% w/w) to form solutions having a precursor concentration of about 10% w/w. The first and second precursor were used in a weight ratio to provide an approximately equivalent number of SG and amine functional end groups in each solution. The initial pH of Study System 1 was 2.91 and the initial pH of Study System 2 was 5.21. The precursors in the Study Systems dissolved rapidly in the WFI, as determined by the absence of particulates upon visual inspection. Rapid gelation occurred upon forming solution CS-1. The pH of the comparative system was unable to be measured before gelation.

TABLE 1

| System | First Precursor | Second Precursor | Solvent | Initial pH |
|---|---|---|---|---|
| Study System 1 | 8A15k PEG SG (0.4282 g) | 8A20k PEG amine-HCl (0.5714 g) | WFI (9 g) | 2.91 |
| Comparative System 1 (CS-1) | 8A15k PEG SG (0.4286 g) | 8A20k PEG amine (0.5727 g) | WFI (9 g) | * |
| Study System 2 | 8A15k PEG SG (1.2451 g) | Trilysine (0.148 g) | WFI (9 g) | 5.21 |

* system pH was unable to be measured before gelation

Immediately after dissolution, a pipette was used to deliver a 150 µl aliquot of Study System 1 into a 50 µl aliquot of phosphate buffered saline (PBS) at 37° C. The process was repeated two additional times for a total of three samples. Gelation was evaluated visually based on observing a cohesive bullous formed around a spinning micro stir bar. The time to gelation for each sample at 0 minutes after dissolution was recorded as shown in Table 2. The average gel time was 23.11 seconds. At 30 minutes, 60 minutes, and 90 minutes after dissolution, the procedure was repeated. Similarly, immediately after dissolution, a pipette was used to deliver a 150 µl aliquot of Study System 2 into a 50 µl aliquot of phosphate buffered saline (PBS) at 37° C. The process was repeated with a second sample. As shown in Table 2, the time to gelation was 101.75 seconds (for sample 1 and 101.44 seconds for sample 2. The average gel time at 0 minutes after dissolution for Study System 2 was 101.60 seconds (about 1.7 minutes), which is significantly longer than the average gel time of 23.11 seconds for Study System 1. At 30 minutes after preparation, a first sample of Study System 2 was tested, however, the gel time results are suspect due to the presence of gel in the solution during pipetting. Pipetting of a second 150 µl aliquot of Study System 2 was not possible due to the presence of gel. Correspondingly, samples were unable to be taken at 60 and 90 minutes, as indicated in Table 2. Pipetting of a 150 µl aliquot of CS-1 was also not possible due to the presence of gel.

TABLE 2

| System | Sample Number | Gel time for system tested at 0 min after dissolution | Gel time for system tested at 30 min after dissolution | Gel time for system tested at 60 min after dissolution | Gel time for system tested at 90 min after dissolution |
|---|---|---|---|---|---|
| Study System 1 | 1 | 23.19 sec | 27.19 sec | 35.63 sec | 39.31 sec |
|  | 2 | 24.75 sec | 34.13 sec | 42.68 sec | 46.07 sec |
|  | 3 | 21.38 sec | 33.18 sec | 43.38 sec | 47.87 sec |
| CS-1 | 1 | N/A[1] | N/A[1] | N/A[1] | N/A[1] |
| CS-2 | 1 | 101.75 sec | 11.93 sec[2] | N/A[1] | N/A[1] |
|  | 2 | 101.44 sec | N/A[1] | N/A[1] | N/A[1] |

[1]Presence of gel did not allow pipetting of the sample.
[2]Gel was present during pipetting of the sample.

A comparison of Study System 1 with CS-1 shows that substituting a non-salted version of the second precursor resulted in gel forming instantly upon preparation. CS-1 showed no storage stability. A comparison of Study System 1 with Study System 2 shows that substituting the second precursor with trilysine resulted in a storage stability of less than 30 minutes and a significantly increased gel time when tested immediately after dissolution. This study showed that only Study System 1 had a storage stability of more than 30 minutes after preparation. Additionally, Study System 1 had gel times of less than 30 seconds. This study further showed that Study System 1 had a storage stability of more than 90 minutes and throughout this storage period, the gel times did not exceed 50 seconds.

Example 3: In Vitro Performance Study for Systems with Buffer

This example demonstrates the effect of buffer on the performance of a single component system.

A single component system (Study System 1B) was prepared from the first precursor and second precursor of Study System 1 of Example 2. For Study System 1B, the precursors were dissolved in a 0.01 M pH 4.01 sodium phosphate monobasic buffer solution instead of WFI, as shown in Table 3. The precursors, in the form of dry powders, were combined with the buffer solution and a trace amount of FD&C Blue #1 (less than about 0.011% w/w) to form a solution having a precursor concentration of about 10% w/w. The first and second precursor were used in a weight ratio to provide an approximately equivalent number of SG and amine functional end groups in each solution. The initial pH of Study System 1 was 2.91 and the initial pH of Study System 1B was 2.09. For each solution, the precursors dissolved rapidly, as determined by the absence of particulates upon visual inspection.

TABLE 3

| System | First Precursor | Second Precursor | Solvent | Initial pH |
|---|---|---|---|---|
| Study System 1 (from Example 2) | 8A15k PEG SG (0.4282 g) | 8A20k PEG amine-HCl (0.5714 g) | WFI (9 g) | 2.91 |
| Study System 1B | 8A15k PEG SG (0.4272 g) | 8A20k PEG amine-HCl (0.5727 g) | sodium phosphate monobasic buffer solution (9 g) | 2.09 |

Immediately after dissolution, a pipette was used to deliver a 150 µl aliquot of Study System 1B into a 50 µl aliquot of phosphate buffered saline (PBS) at 37° C. The process was repeated two additional times for a total of three samples. The time to gelation for each sample at 0 minutes after dissolution was recorded as shown in Table 4. The average gel time was 48.14 seconds. The gel time is more than double the gel time for Study System 1. The results directly show the effect of using a buffer solution versus (unbuffered) WFI as a solvent for the precursors. At 30 minutes, 60 minutes, and 90 minutes after dissolution of Study System 1B, the procedure was repeated. For each time period tested, Study System 1B showed at least a 45% increase in average gel time.

TABLE 4

| System | Sample Number | Gel time for system tested at 0 min after dissolution | Gel time for system tested at 30 min after dissolution | Gel time for system tested at 60 min after dissolution | Gel time for system tested at 90 min after dissolution |
|---|---|---|---|---|---|
| Study System 1 | 1 | 23.19 sec | 27.19 sec | 35.63 sec | 39.31 sec |
|  | 2 | 24.75 sec | 34.13 sec | 42.68 sec | 46.07 sec |

TABLE 4-continued

| System | Sample Number | Gel time for system tested at 0 min after dissolution | Gel time for system tested at 30 min after dissolution | Gel time for system tested at 60 min after dissolution | Gel time for system tested at 90 min after dissolution |
|---|---|---|---|---|---|
| | 3 | 21.38 sec | 33.18 sec | 43.38 sec | 47.87 sec |
| | AVG | 23.11 sec | 31.50 sec | 40.56 sec | 44.42 sec |
| Study System 1B | 1 | 48.06 sec | 28.94 sec | 56.43 sec | 61.13 sec |
| | 2 | 48.19 sec | 53.88 sec | 60.19 sec | 67.18 sec |
| | 3 | 48.18 sec | 54.62 sec | 60.75 sec | 71.25 sec |
| | AVG | 48.14 sec | 45.81 sec | 59.12 sec | 66.52 sec |

This study showed that Study System 1B had a storage stability of more than 90 minutes after preparation and throughout this storage period, the average gel times did not exceed 70 seconds. The results indicate that buffer may be used with the systems described in this invention, but the addition of buffer does not seem to provide superior or even equivalent results to systems prepared with WFI.

Example 4: Effect of Buffer Concentration on In Vitro Performance

This example demonstrates the effect of buffer concentration and system pH on the performance of a single component system.

A single component system (Study System 1C) was prepared from the first precursor and second precursor of Study System 1 of Example 2. For Study System 1C, the precursors were dissolved in a 0.01 M pH 4.01 sodium phosphate monobasic buffer solution, as shown in Table 5. The precursors, in the form of dry powders, were combined with the buffer solution and a trace amount of FD&C Blue #1 (less than about 0.011% w/w) to form a solution having a precursor concentration of about 10% w/w. The first and second precursor were used in a weight ratio to provide an approximately equivalent number of SG and amine functional end groups in each solution. The precursors dissolved rapidly, as determined by the absence of particulates upon visual inspection. The initial pH of Study System-C was 2.92.

TABLE 5

| System | First Precursor | Second Precursor | Solvent |
|---|---|---|---|
| Study System 1C | 8A15k PEG SG (0.4282 g) | 8A20k PEG amine-HCl (0.5738 g) | sodium phosphate monobasic buffer solution (8 g) |

Immediately after dissolution, a pipette was used to deliver a 150 µl aliquot of Study System 1C into a 50 µl aliquot of phosphate buffered saline (PBS) at 37° C. The process was repeated with a second sample. The pH of Study System 1C and the time to gelation for each sample after dissolution was recorded as shown in Table 6. A 250 µL aliquot of concentrated monobasic phosphate (0.0121 g monobasic/mL; pH 4.30) was added to the vial containing Study System 1C. The pH was measured. The gel time of the resulting solution was measured as described above. Additional aliquots of the concentrated monobasic solution were added as shown in Table 6. The pH and gel time were measured after each addition. The results shown in Table 6 are plotted in FIG. 5 as the gel time (left axis) and the amount of added concentrated monobasic ("dilution amount," right axis) as a function of system pH.

TABLE 6

| System | pH | Gel time, seconds |
|---|---|---|
| Study System 1C | 2.92 | 51.00 |
| | | 52.75 |
| Study System 1C with 250 µL of concentrated monobasic | 2.97 | 60.68 |
| | | 65.32 |
| Study System 1C with 500 µL of concentrated monobasic | 3.01 | 72.00 |
| | | 71.00 |
| Study System 1C with 750 µL of concentrated monobasic | 3.03 | 86.38 |
| | | 86.25 |
| Study System 1C with 1250 µL of concentrated monobasic | 3.16 | 114.37 |
| | | 115.57 |
| Study System 1C with 1750 µL of concentrated monobasic | 3.24 | 149.56 |
| | | 148.56 |
| Study System 1C with 2250 µL of concentrated monobasic | 3.29 | 186.13 |
| | | 189.68 |
| Study System 1C with 2750 µL of concentrated monobasic | 3.35 | 264.94 |
| | | 273.38 |

Figure 5:
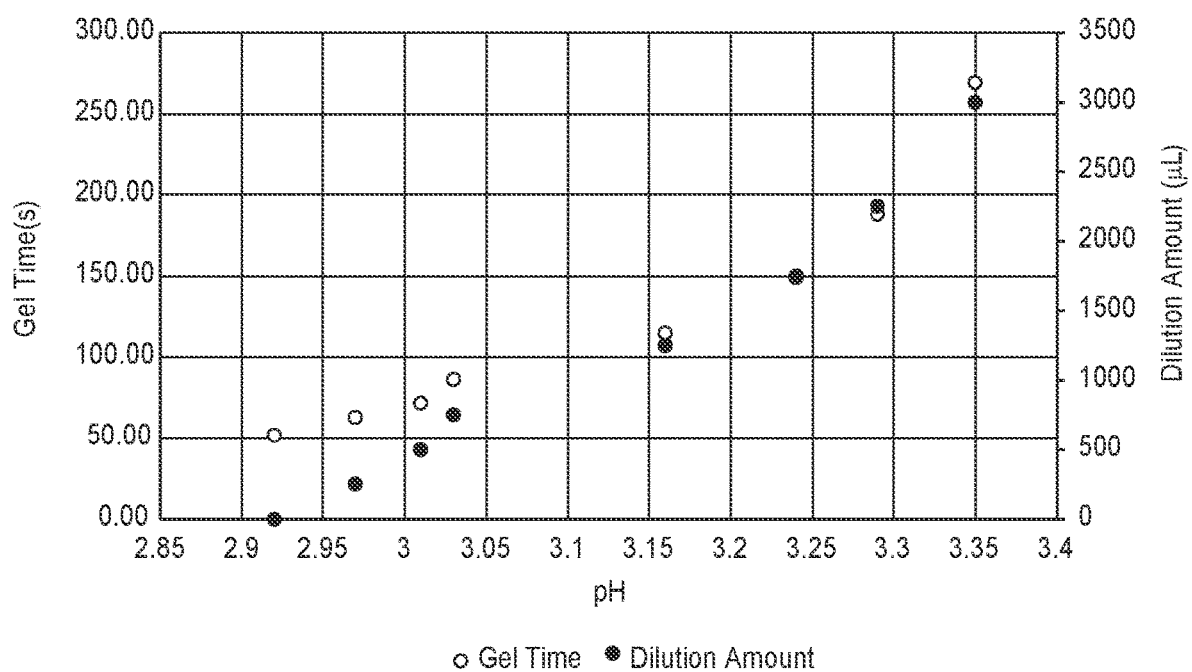
FIG. 5. is a plot of gel time and dilution volume as a function of pH for a single solution system with added buffer.

FIG. 5 shows that the gel time increases non-linearly with pH. At the initial pH of 2.92 the average gel time was about 51.88 seconds. At pH 3.16, the average gel time was more than doubled at 114.97 seconds. At pH 3.35, the average gel time was 269.16 seconds (about 4.5 minutes) and more than 5 times the gel time of the Study System 1C solution. The results suggest that the gel time is more affected by the presence of the buffer as the pH as the solution approaches the pH buffering range of the buffer. Significantly, the single solution systems of this example did not show storage stability limitations over the pH ranges studied.

This study showed that a range of buffer concentrations and pH may be used with the precursors described in this invention, but the addition of buffer (and associated changes in pH) have the effect of increasing the gel time, especially as the pH range of the buffer is approached. These results nicely demonstrate the buffer effect since gelation involves a raising of the pH to deprotonate the amine, but a buffered system, with an initially higher pH, gels significantly more slowly.

Example 5: Subcutaneous Performance Study

This example evaluated the effect of precursor concentration on the performance of a single component system via an in vivo model. Efficacy of the single component system for performing repeated subcutaneous injections along a tissue was also evaluated.

Three concentrations of the single component system described in Example 1 were prepared to form a 10% w/w solution, a 20% w/w solution, and a 30% w/w solution. For each solution, the precursors dissolved rapidly in the WFI, as determined by visual inspection. Immediately after dissolution, each prepared solution was drawn into a separate 5 ml syringe and affixed with a separate 25 gauge needle. Approximately 500 µl of each of the three solutions was injected subcutaneously into a sedated pig (65 kg in weight) at separate but similar sites along the porcine abdomen. It was observed that the 10% and the 20% solutions formed distinct gel pockets that could be felt as a hard subcutaneous masses at about 10-30 seconds after injection. At 1 minute after injection, each injection site was dissected. The sites of injection of the 10% and 20% solutions showed the presence of blue gels. The site of injection of the 30% solution upon dissection revealed blue fluid which oozed out of the subcutaneous placement site, indicating that a gel had not formed. The 30% solution was observed to gel within the dissected placement site after a period of 2 minutes. The results suggest an upper concentration limit for achieving gel formation with a single component system.

Following the initial study, the original 10% solution (with original syringe and needle) was used to make a series of closely spaced subcutaneous injections into the porcine urethra. Each injection delivered a volume of approximately 250 µl. The injections proceeded for a period of 5 minutes during which time no evidence of clogging of the needle was observed. The presence of gel at the injection site after a period of 10-30 seconds was confirmed by pressing/squeezing the tissue. A series of beads of hard subcutaneous mass could be felt indicating that the repeated injections formed interconnecting gel.

This study showed that the single component system is concentration dependent and can be effectively used with a small gauge needle to perform repeated subcutaneous injections which form gel within 10-30 seconds.

Example 6: Multi-Site Performance Study

This example evaluated a single component system for sequential use at multiple locations of an in vivo model.

A 10% w/w solution was prepared according to Example 1 with the modification that a small amount (less than 0.001%) of Fluorescein-NHS was added to the solution. Immediately after dissolution, the prepared solution was drawn into a 5 ml syringe and affixed with a 30 gauge needle.

Part A: Subcutaneous Injection Site

Approximately 500 µl of the solution was injected subcutaneously into the subcutaneous tissue of a freshly euthanized pig (65 kg in weight). Gel was firm and intact by feel under the dermis in less than 10 seconds. At 1 minute after injection, the injection site was dissected and evaluated under blue light. The presence of the gel formed a raised bump on the surface of the outer epidermis. The gel could be visualized through the outer epidermis, showing that the gel was a slightly oblong and flattened sphere shape with a radius of about 15 mm. The dissection confirmed the presence of a gel and its size and shape.

Part B: Subconjunctival Injection Site

Using the same solution, syringe, and needle from Part A, approximately 200 µl of the solution was injected subconjunctiva into an eye of the pig from Part A. After injection, the injection site was visualized under blue light. Gel was firm and intact by feel under the dermis in less than 10 seconds.

Part C: Periodontal Injection Sites

Using the same solution, syringe, and needle from Parts A and B, an approximate aliquot of 250 µl of the solution was injected multiple times below the gums of the pig from Parts A and B. After injection, the injection sites were visualized under blue light which showed the presence of multiple small gel depots. Gel was firm and intact by feel under the dermis in less than 10 seconds.

This study showed that a single solution, syringe, and needle can be used to deliver a hydrogel depot to multiple locations of the body over a period of about an hour. During this period, the time to gelation remained at about 10-30 seconds. The study also showed that a contrast agent can be used to visualize the size and location of a hydrogel through the dermis of various tissues.

Example 7: Multi-Site Ocular Performance Study

This example evaluated a single component system for sequential use at multiple ocular locations of an in vivo model.

A 10% w/w solution was prepared according to Example 6. Immediately after dissolution, the prepared solution was drawn into a 5 ml syringe and affixed with a 30 gauge needle.

Part A: Eyelid Injection Site

Discrete 50 µl aliquots of the solution were injected into each of five locations across the eyelid margin of a freshly euthanized pig (65 kg in weight). The injection sites were visualized under blue light and with a yellow filter which showed the presence of multiple small gel depots across the eyelid. Gel was firm and intact by feel under the dermis in less than 10 seconds.

Part B: Anterior Chamber Injection Site

Using the same solution, syringe, and needle from Part A, approximately 100 µl of the solution was injected into the anterior chamber of an eye of the pig from Part A. The injection site was visualized under blue light with a yellow filter. Gel was determined to be solid after 10 seconds as the Fluorescein-NHS dye did not dissipate or migrate through the aqueous humor.

This study showed that a single solution, syringe, and needle can be used to deliver a hydrogel depot to multiple ocular locations via a small gauge needle, including repeated injections along a lash line and injections into the anterior chamber, without clogging of the needle. In this study, the solution was used to successfully perform injections over a period of about 1 hour and during this period, the time to gelation remained at about 10-30 seconds.

Example 8: Multi-Site Skin Injection Study

This example evaluated a single component system for sequential use at multiple skin locations of an in vivo model.

A 10% w/w solution was prepared according to Example 6. Immediately after dissolution, the prepared solution was drawn into a 5 ml container of a commercially available tattoo device (i.e. gun).

Part A: Subcutaneous Injection

A continuous line of the solution was injected across the inner abdomen of a freshly euthanized pig (65 kg in weight). The injection sites were visualized under blue light and with a yellow filter which showed the presence of continuous line of gel depots across the abdominal skin of the pig. Gel was evident and non migratory, able to be visualized under fluorescent light.

Additional Inventive Concepts

1. A method for instilling an in situ crosslinked hydrogel into a patient's fallopian tubes, the method comprising:
   sequentially delivering a hydrogel precursor solution with an applicator directly into a first fallopian tube of a patient followed by delivery into a second fallopian tube of the patient, wherein the applicator comprises a reservoir of the hydrogel precursor solution connected to a catheter configured for transcervical placement of the hydrogel precursor within a fallopian tube, and wherein the hydrogel precursor solution comprises mixture of a first compound with a plurality of electrophilic groups, a second compound with a plurality of nucleophilic groups, and an aqueous solvent at a pH of no more than about 6, wherein the hydrogel precursor solution gels in contact with the tissue of the first fallopian in no more than about 3 minutes and gels in contact with the tissue of the second fallopian tube in no more than about 3 minutes.

2. The method of additional inventive concept 1 wherein the delivering is guided by x-ray, ultrasound, or other medical imaging.

3. The method of additional inventive concept 1 wherein the catheter configured for transcervical placement comprises a balloon, wherein the balloon may be inflated after placement of the catheter in the opening to a fallopian tube and before delivering of the hydrogel precursor solution.

4. The method of additional inventive concept 1 wherein the first compound comprises a multiarm polyethylene glycol with succinimidyl functional groups and the second compound comprises a multiarm polyethylene glycol with protonated amine functional groups.

5. The method of additional inventive concept 1 wherein the hydrogel precursor solution gels to form a first occlusion in the first fallopian tube and a second occlusion in the second fallopian tube.

6. The method of additional inventive concept 5 wherein the first occlusion and the second occlusion provide reversible or permanent female sterilization.

7. The method of additional inventive concept 1 further comprising performing a tubal patency test after a selected period of time.

8. A method for the delivery of a medical hydrogel for in situ crosslinking, the method comprising:
blending an electrophilic precursor and a nucleophilic precursor with an aqueous solvent at a pH of no more than about 6 to form a precursor solution with a storage stability against restriction of flowability of at least about 10 minutes at room temperature as determined by the precursor solution being injectable from a 5 ml syringe with a 25 gauge needle; and
delivering a quantity of the precursor solution to a patient wherein the precursor solution contacts physiological fluids associated with vital physiological tissue to induce crosslinking of the hydrogel, wherein the hydrogel gels in vivo in no more than about 5 minutes.

9. The method of inventive concept 8 wherein the electrophilic precursor and the nucleophilic precursor are powders.

10. The method of inventive concept 8 wherein the electrophilic precursor comprises a first hydrophilic polymer core and a plurality of electrophilic functional groups, wherein the nucleophilic precursor comprises a second hydrophilic polymer core and a plurality of protonated amine groups, and wherein the electrophilic precursor and the nucleophilic precursor are water soluble.

11. The method of inventive concept 8 wherein the electrophilic precursor and the nucleophilic precursor independently have a molecular weight of about 2K Da to about 50K Da and from 4 to 8 arms.

12. The method of inventive concept 11 wherein the plurality of electrophilic functional groups comprise a reactive ester.

13. The method of inventive concept 11 wherein the first hydrophilic polymer core and/or the second hydrophilic polymer core comprise polyethylene glycol, polyvinyl alcohol, polylactic acid, polyoxazoline, copolymers thereof, or mixtures thereof.

14. The method of inventive concept 8 further comprising an additional electrophilic precursor and/or an additional nucleophilic precursor.

15. The method of inventive concept 8 wherein the precursor solution further comprises a therapeutic agent and/or a visualization agent comprising a coloring agent, a fluorescent molecule, an ultrasonic contrast agent, a x-ray contrast agent, an MRI contrast agent, or a combination thereof.

16. The method of inventive concept 8 wherein the precursor solution has a storage stability against restriction of flowability of at least about 2 hours at room temperature as determined by the precursor solution being injectable from a 5 ml syringe with a 25 gauge needle.

17. The method of inventive concept 8 further comprising delivering a quantity of precursor solution to one or more additional patients to form one or more additional hydrogels, wherein the one or more additional hydrogels individually gel in no more than about 3 minutes.

18. The method of inventive concept 8 wherein the delivering comprises injecting through a needle, high pressure needless injecting, delivering through a catheter, delivering with a dropper, or spraying.

19. The method of inventive concept 8 wherein the delivering comprises multiple injections from a single barrel syringe wherein the same needle is used or the needle is changed between injections or a combination thereof.

20. The method of inventive concept 8 further comprising assigning an expiration time after blending and discarding after the expiration time expires.

21. The method of inventive concept 8 wherein the vital physiological tissue comprises an immunologically privileged space, a subcutaneous location, an ocular location, an intramural location, a body lumen, an abnormal tissue, a target tissue, or a combination thereof.

22. The method of inventive concept 8 wherein the delivering is to a tumor, a fallopian tube, a uterus, a urethra, a blood vessel, an intramuscular location, a location between a muscle and a nerve, an eye lash line, or in and around the eye.

23. The method of inventive concept 8 wherein the delivering is monitored using a visualization agent.

24. The method of inventive concept 8 wherein the hydrogel gels in no more than 30 seconds.

25. The method of inventive concept 8 wherein the hydrogel degrades in no more than about 14 days.

26. The method of inventive concept 8 wherein the hydrogel releases a therapeutic amount of a therapeutic agent.

27. The method of inventive concept 26 wherein the therapeutic agent comprises a pain reliever, an anesthetic, a steroid, a chemotherapeutic agent, a glycosaminoglycan, a carbohydrate, a nucleic acid, a protein, an anti-tumor drug, a glaucoma drug, an antibiotic, an enzyme, an anti-infective, an antifungal, an anti-inflammatory drug, a non-steroidal anti-inflammatory drug, an antineoplastic agent, a hormone, an angiogenic agent, an anti-angiogenic agent, a growth factor, an intraocular pressure-lowering agent, an antibody, a neurotransmitter, a psychoactive drug, an anticancer drug, a drug affecting reproductivity, genes, cells, a cellular product, an oligonucleotide, or combinations thereof.

28. The method of inventive concept 8 wherein the hydrogel releases a therapeutic amount of a therapeutic agent for up to about 14 days.

29. The method of inventive concept 8 wherein the hydrogel releases a therapeutic amount of a therapeutic agent for up to about 180 days.
30. The method of inventive concept 8 wherein the hydrogel releases a therapeutic amount of a therapeutic agent for at least about 180.
31. The method of inventive concept 8 wherein the hydrogel degrades in no more than about 14 days.
32. The method of inventive concept 8 wherein the hydrogel degrades in no more than about 180 days.
33. The method of inventive concept 8 wherein the hydrogel persists for at least about 180 days.
34. The method of inventive concept 8 wherein the multiple injections are made to form a tattoo based on an aesthetic design.
35. The method of inventive concept 34 wherein the hydrogel comprises covalently bonded dye.
36. The method of inventive concept 34 wherein the hydrogel persists for no more than about 180 days.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein. To the extent that specific structures, compositions and/or processes are described herein with components, elements, ingredients or other partitions, it is to be understood that the disclosure herein covers the specific embodiments, embodiments comprising the specific components, elements, ingredients, other partitions or combinations thereof as well as embodiments consisting essentially of such specific components, ingredients or other partitions or combinations thereof that can include additional features that do not change the fundamental nature of the subject matter, as suggested in the discussion, unless otherwise specifically indicated.

What is claimed is:

1. A medical hydrogel precursor solution comprising a mixture of an aqueous solvent at a pH of no more than about 6, a first precursor comprising a plurality of electrophilic functional groups and a first hydrophilic core, and a second precursor comprising a plurality of protonated amine groups, wherein the precursor solution is flowable ex vivo for at least 10 minutes after formation and has a simulated in situ gel time of no more than 5 minutes, wherein the simulated in situ gel time is measured in vitro by injecting a volume of the precursor solution at room temperature into a ⅓ volume of phosphate buffered saline (PBS) at 37° C., maintaining the combined volumes at 37° C., and recording the time until a solid or a semi-solid mass is formed, wherein the volume of the precursor solution and the volume of PBS are equal.
2. The medical hydrogel precursor solution of claim 1 wherein the simulated in situ gel time is no more than about 3 minutes.
3. The medical hydrogel precursor solution of claim 1 wherein the simulated in situ gel time is about 10-40 seconds.
4. The medical hydrogel precursor solution of claim 1 having a storage stability against restriction of flowability of at least about 10 minutes at room temperature as determined by the precursor solution being injectable from a 5 ml syringe with a 27 gauge needle.
5. The medical hydrogel precursor solution of claim 1 having no more than about 0.025M added buffer and having a storage stability against restriction of flowability of at least about 2 hours at room temperature as determined by the precursor solution being injectable from a 5 ml syringe with a 25 gauge needle.
6. The medical hydrogel precursor solution of claim 1 wherein the aqueous solvent has no added buffer.
7. The medical hydrogel precursor solution of claim 1 wherein the aqueous solvent consists essentially of unbuffered saline or water for injection.
8. The medical hydrogel precursor solution of claim 1 wherein the first hydrophilic core and/or the second hydrophilic core comprise a polymer.
9. The medical hydrogel precursor solution of claim 1 wherein the first hydrophilic core and/or the second hydrophilic core comprise polyethylene glycol, polyvinyl alcohol, polyoxazoline, copolymers thereof, or mixtures thereof.
10. The medical hydrogel precursor solution of claim 1 wherein the first hydrophilic core has a plurality of arms having electrophilic functional groups, the second hydrophilic core has a plurality of arms having protonated amine groups, or a combination thereof.
11. The medical hydrogel precursor solution of claim 10 wherein the plurality of arms is from 3 to 8.
12. The medical hydrogel precursor solution of claim 1 wherein the molecular weight of the second precursor is greater than or equal to the molecular weight of the first precursor.
13. The medical hydrogel precursor solution of claim 1 wherein the first precursor and the second precursor independently have a molecular weight of about 2K Da to about 50K Da and from 3 to 8 arms.
14. The medical hydrogel precursor solution of claim 1 wherein the electrophilic functional groups comprise a reactive ester.
15. The medical hydrogel precursor solution of claim 1 wherein the electrophilic functional groups comprise succinimidyl succinate, succinimidyl succinamide, succinimidyl glutarate, succinimidyl glutaramide, succinimidyl adipate, succinimidyl azelate, or a combination thereof.
16. The medical hydrogel precursor solution of claim 1 wherein the electrophilic functional groups have a degradable ester linkage to the first hydrophilic core or a non-degradable amide linkage to the first hydrophilic core.
17. The medical hydrogel precursor solution of claim 1 wherein the precursor solution has a solids concentration of at least about 1 wt %.
18. The medical hydrogel precursor solution of claim 1 wherein the precursor solution has a solids concentration of no more than about 30 wt %.
19. The medical hydrogel precursor solution of claim 1 wherein the precursor solution has a solids concentration of about 8 wt % to about 17 wt %.
20. The medical hydrogel precursor solution of claim 1 further comprising a therapeutic agent.
21. The medical hydrogel precursor solution of claim 20 wherein the therapeutic agent comprises a pain reliever, an anesthetic, a steroid, a chemotherapeutic agent, a glycosaminoglycan, a carbohydrate, a nucleic acid, a protein, an anti-tumor drug, a glaucoma drug, an antibiotic, a steroid, an enzyme, an anti-infective, an antifungal, an anti-inflammatory drug, a non-steroidal anti-inflammatory drug, an anti-neoplastic agent, a hormone, an angiogenic agent, an anti-angiogenic agent, a growth factor, an intraocular pressure-lowering agent, an antibody, a neurotransmitter, a psychoactive drug, an anticancer drug, a drug affecting reproductivity, genes, cells, an oligonucleotide, or combinations thereof.

22. The medical hydrogel solution of claim 20 wherein the therapeutic agent comprises travoprost, a prostaglandin analogue, a low-soluble prostaglandin analogue, a mydriatic agent, an anti-VEGF agent, an anti-VEGFR1 agent, an anti-VEGFR2 agent, an anti-VEGFR3 agent, an anti-PDGF agent, an anti-PDGF-R agent, an anti-PDGFRβ agent, sunitinib, E7080, takeda-6d, tivozanib, regorafenib, sorafenib, pazopanib, axitinib, nintedanib, cediranib, vatalanib, motesanib, macrolides, sirolimus, everolimus, a tyrosine kinase inhibitor, imatinib, gefitinib, toceranib, erlotinib, lapatinib, nilotinib bosutinib neratinib, lapatinib, vatalanib, dexamethasone, moxifloxacin, nepafenac, a macrolide, rapamycin, sirolimus, tacrolimus, lipoic acid and derivatives, sterols, oxysterols, mRNA, chimeric antigen receptor cells, T cells, NK cells, genetically modified T cells, stem cells, pancreatic cells, or combinations thereof.

23. The medical hydrogel solution of claim 20 wherein the therapeutic agent comprises mRNA, chimeric antigen receptor cells, T cells, NK cells, genetically modified T cells, stem cells, pancreatic cells, or combinations thereof.

24. The medical hydrogel precursor solution of claim 1 further comprising a visualization agent.

25. The medical hydrogel precursor solution of claim 24 wherein the visualization agent is biocompatible and comprises a coloring agent, a fluorescent molecule, a contrast agent, or a combination thereof.

26. The medical hydrogel precursor solution of claim 25 wherein the visualization agent is covalently bonded to the first precursor, the second precursor, or a combination thereof.

27. The medical hydrogel precursor solution of claim 25 wherein the visualization agent comprises a reactive functional group that can react with the nucleophilic functional group of the second precursor at an appropriate pH.

28. The medical hydrogel precursor solution of claim 1 further comprising a third precursor comprising a third hydrophilic core and a plurality of functional groups, wherein the plurality of functional groups comprise electrophilic functional groups or protonated amine groups.

29. The medical hydrogel precursor solution of claim 1 wherein a hydrogel formed from the precursor solution has a simulated in situ degradation time of no more than about 14 days, wherein the simulated in situ degradation time is measured in vitro by injecting a volume of the precursor solution at room temperature into a volume of PBS at 37° C., maintaining the combined volumes at 37° C., and recording the time from the formation of a solid or a semi-solid mass until the disappearance of the solid or the semi-solid mass, wherein the volume of the precursor solution and the volume of PBS are equal.

30. The medical hydrogel precursor solution of claim 1 wherein a hydrogel formed from the precursor solution has a simulated in situ degradation time of no more than about 180 days, wherein the simulated in situ degradation time is measured in vitro by injecting a volume of the precursor solution at room temperature into a volume of PBS at 37° C., maintaining the combined volumes at 37° C., and recording the time from the formation of a solid or a semi-solid mass until the disappearance of the solid or the semi-solid mass, wherein the volume of the precursor solution and the volume of PBS are equal.

31. The medical hydrogel precursor solution of claim 29 wherein a visualization agent is covalently bonded to the first precursor, the second precursor, or a combination thereof.

32. The medical hydrogel precursor solution of claim 1 wherein a hydrogel formed from the precursor solution has a simulated in situ degradation time of at least about 180 days, wherein the simulated in situ degradation time is measured in vitro by injecting a volume of the precursor solution at room temperature into a volume of PBS at 37° C., maintaining the combined volumes at 37° C., and recording the time from the formation of a solid or a semi-solid mass until the disappearance of the solid or the semi-solid mass, wherein the volume of the precursor solution and the volume of PBS are equal.

33. The medical hydrogel precursor solution of claim 1 wherein the aqueous solvent is unbuffered saline or water for injection.

34. A medical hydrogel precursor solution comprising a mixture of an aqueous solvent at a pH of no more than about 6 with no added buffer, such that only buffer present is from impurities and/or dissolved carbon dioxide, a first precursor comprising a plurality of electrophilic functional groups and a first hydrophilic core, and a second precursor comprising a plurality of protonated amine groups and a second hydrophilic core.

35. The medical hydrogel precursor solution of claim 34 further comprising a visualization agent.

36. A dispenser comprising the medical hydrogel precursor solution of claim 1.

37. The dispenser of claim 36 wherein the dispenser comprises a needle and syringe.

38. The dispenser of claim 36 wherein the dispenser comprises a dropper.

39. The dispenser of claim 36 wherein the dispenser comprises a catheter.

40. The dispenser of claim 36 wherein the dispenser comprises a tattoo device.

* * * * *

UNITED STATES PATENT AND TRADEMARK OFFICE
CERTIFICATE OF CORRECTION

PATENT NO. : 12,251,466 B2
APPLICATION NO. : 17/725361
DATED : March 18, 2025
INVENTOR(S) : Bassett et al.

Page 1 of 1

It is certified that error appears in the above-identified patent and that said Letters Patent is hereby corrected as shown below:

In the Claims

In Column 43, Claim 22, Line 4, after "hydrogel" insert -- precursor --.

In Column 43, Claim 22, Line 14, delete "nilotinib bosutinib neratinib," and insert -- nilotinib, bosutinib, neratinib, --, therefor.

In Column 43, Claim 23, Line 20, after "hydrogel" insert -- precursor --.

Signed and Sealed this
Thirtieth Day of September, 2025

John A. Squires
*Director of the United States Patent and Trademark Office*